United States Patent
Yun et al.

(10) Patent No.: US 10,305,043 B2
(45) Date of Patent: May 28, 2019

(54) COMPOUND FOR ORGANIC ELECTRONIC ELEMENT, ORGANIC ELECTRONIC ELEMENT USING THE SAME, AND ELECTRONIC DEVICE THEREOF

(71) Applicant: DUK SAN NEOLUX CO., LTD., Cheonan-si, Chungcheongnam-do (KR)

(72) Inventors: Jin Ho Yun, Cheonan-si (KR); Sun Hee Lee, Hwaseong-si (KR); Nam Jin Park, Cheonan-si (KR); Yun-sun Byun, Daegu (KR); Daesung Kim, Yongin-si (KR); Soung Yun Mun, Cheonan-si (KR); Bum Sung Lee, Hwaseong-si (KR); Jae-Taek Kwon, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 22 days.

(21) Appl. No.: 15/162,835

(22) Filed: May 24, 2016

(65) Prior Publication Data
US 2017/0084843 A1    Mar. 23, 2017

(30) Foreign Application Priority Data
Sep. 17, 2015    (KR) .................. 10-2015-0131326

(51) Int. Cl.
| | |
|---|---|
| *H01L 51/00* | (2006.01) |
| *C07D 307/91* | (2006.01) |
| *H01L 51/50* | (2006.01) |
| *H01L 27/32* | (2006.01) |

(52) U.S. Cl.
CPC ........ *H01L 51/0061* (2013.01); *C07D 307/91* (2013.01); *H01L 51/006* (2013.01); *H01L 27/3244* (2013.01); *H01L 51/0052* (2013.01); *H01L 51/0058* (2013.01); *H01L 51/0073* (2013.01); *H01L 51/5096* (2013.01)

(58) Field of Classification Search
CPC .............. H01L 51/0061; H01L 51/006; H01L 51/5096; H01L 51/0073; H01L 51/0052; H01L 51/0058
See application file for complete search history.

(56) References Cited

U.S. PATENT DOCUMENTS

2016/0118596 A1*  4/2016  Sakamoto ............ H01L 51/006
                                                                    257/40

FOREIGN PATENT DOCUMENTS

| KR | 10-2011-0011647 A | 2/2011 |
|---|---|---|
| KR | 10-2011-0081274 A | 7/2011 |
| KR | 10-2013-0028673 A | 3/2013 |
| KR | 10-2014-0087882 A | 7/2014 |
| KR | 10-2015-0006374 A | 1/2015 |
| KR | 10-1493482 B1 | 2/2015 |

(Continued)

OTHER PUBLICATIONS

The Prior Art Search Report in priority application KR 10-2015-0131326, dated Apr. 28, 2016, five pages.

*Primary Examiner* — Golam Mowla
(74) *Attorney, Agent, or Firm* — Vorys, Sater, Seymour & Pease LLP; Mih Suhn Koh

(57) ABSTRACT

The present invention provides a novel compound for an EBL capable of improving the light emitting efficiency, stability and life span of a device, and an organic electric element and an electronic device using the same.

9 Claims, 2 Drawing Sheets
(1 of 2 Drawing Sheet(s) Filed in Color)

(56) References Cited

FOREIGN PATENT DOCUMENTS

| KR | 10-2015-0021771 A | 3/2015 |
|----|-------------------|--------|
| WO | 2014/104515 A1 | 7/2014 |

\* cited by examiner

COMPOUND FOR ORGANIC ELECTRONIC ELEMENT, ORGANIC ELECTRONIC ELEMENT USING THE SAME, AND ELECTRONIC DEVICE THEREOF

FIELD OF THE INVENTION

The present invention relates to compound for organic electronic element, organic electronic element using the same, and an electronic device thereof.

DESCRIPTION OF THE RELATED ART

Recently, in an organic light emitting diode (OLED), researches on adding an electron blocking layer (EBL) between a hole transport layer and an emission layer are continuously conducted to solve defects on light emission at the interface of the hole transport layer and on the decrease of efficiency due to charge unbalance in the emission layer. Particularly, developments on different electron blocking materials (EBM) according to respective emission layer (R, G, B) are conducted.

However, in the case where different EBLs are used for respective emission layer (R, G, B) as described above, various limitations are generated at the point where an OLED panel is being gradually large-sized. Particularly, each of the EBLs is required to be patterned according to emission regions (R, G, B), and the patterning time increases (the number of masks used increases), consuming time for processing increases (exchange time of masks increases), and processing issues accompanied with the mask exchange is generated.

In order to solve the defects generated due to the use of different EBLs according to the emission regions (R, G, B) as described above, developments on EBMs commonly used in the emission regions (R, G, B) are desperately in need. However, due to luminescent materials used in each emission region of an OLED panel currently produced, the development on a common EBM is difficult. The luminescent material used in the OLED panel is largely classified as a phosphorescent luminescent material and a fluorescent luminescent material. For green and red color, the manufacture of a panel having high efficiency and long life may be easy through using the phosphorescent luminescent material, however, for blue color, the development of the phosphorescent luminescent material having high efficiency and long life is difficult, and the fluorescent luminescent material is used now.

SUMMARY OF THE INVENTION

Accordingly, developments on an EBM having both electrical and physical properties required for each of the fluorescent luminescent material and the phosphorescent luminescent material are desperately in need in order to use a common EBL for each emission region (R, G, B).

An object of the present invention is to provide a compound for EBL which is commonly used in each of the emission regions to improve high luminous efficiency, a low driving voltage, a high heat resistance, color purity and life, and an organic electric element and an electronic device using the same.

The present invention provides a compound represented by Formula below.

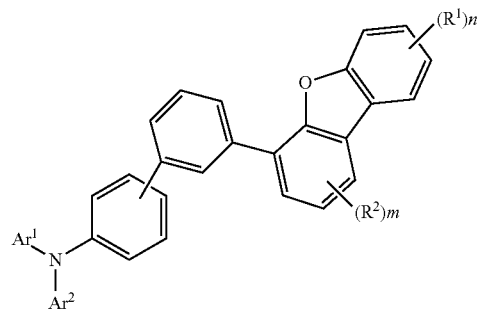

In another aspect of the present invention, the present invention provides organic electric elements using the compound represented by the formula above and electronic devices thereof.

By using the compound according to the present invention to an electron blocking layer (EBL), an organic electric element according to one or more embodiments of the present invention not only has high luminous efficiency, low driving voltage and high heat resistance and, but can also be significantly improved in color purity and life span.

BRIEF DESCRIPTION OF THE DRAWINGS

The patent or application file contains at least one drawing executed in color.

Copies of this patent or patent application publication with color drawing(s) will be provided by the Office upon request and payment of the necessary fee.

DETAILED DESCRIPTION OF THE INVENTION

Figure 1:
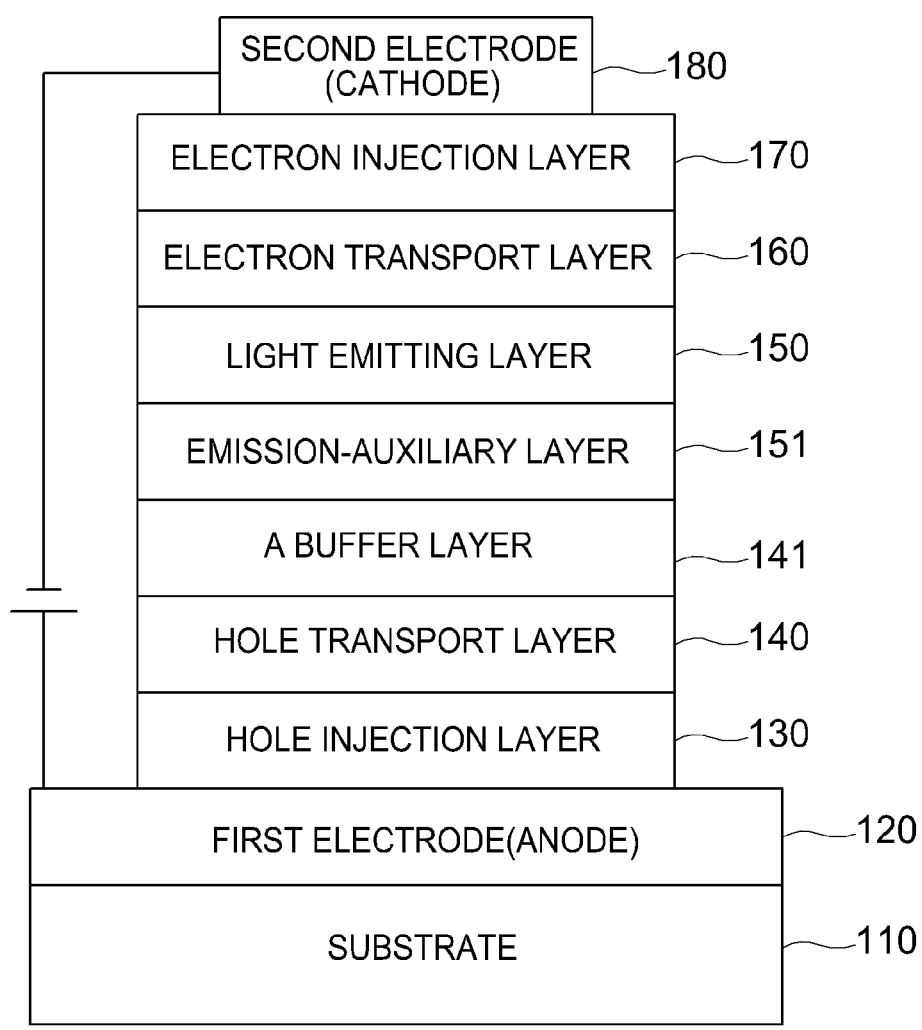
FIG. 1 illustrates an example of an organic light emitting diode according to the present invention.

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component. In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

As used in the specification and the accompanying claims, unless otherwise stated, the following is the meaning of the term as follows.

Unless otherwise stated, the term "halo" or "halogen" as used herein includes fluorine, bromine, chlorine, or iodine.

Unless otherwise stated, the term "alkyl" or "alkyl group" as used herein has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "haloalkyl" or "halogen alkyl" as used herein means an alkyl group substituted with a halogen.

Unless otherwise stated, the term "alkenyl" or "alkynyl" as used herein has, but not limited to, double or triple bonds of 2 to 60 carbon atoms, and includes a linear or a branched chain group.

Unless otherwise stated, the term "cycloalkyl" as used herein means, but not limited to, alkyl forming a ring having 3 to 60 carbon atoms.

Unless otherwise stated, the term "alkoxy group" or "alkyloxy group" as used herein means an oxygen radical attached to an alkyl group, but not limited to, and has 1 to 60 carbon atoms.

Unless otherwise stated, the term "aryloxyl group" or "aryloxy group" as used herein means an oxygen radical attached to an aryl group, but not limited to, and has 6 to 60 carbon atoms.

Unless otherwise stated, the term "fluorenyl group" or "fluorenylene group" as used herein means a monovalent or divalent functional group in the following structure in which all R, R' and R" are hydrogen, and the term "substituted fluorenyl group" or "substituted fluorenylene group" means that at least one of R, R' and R" is a substituent other than hydrogen and includes a case of combining R and R' to each other and forming a spiro compound along with a carbon atom making the combination.

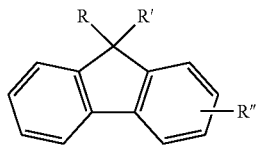

Unless otherwise stated, the term "aryl group" or "arylene group" as used herein has, but not limited to, 6 to 60 carbon atoms. In the present invention, aryl or arylene includes a monocycle, ring assemblies, a fused ring system, a spiro compound, etc.

Unless otherwise stated, the term "heterocyclic group" as used herein includes a non-aromatic ring as well as an aromatic ring such as "heteroaryl group" and "heteroarylene group" and each means, but not limited to, a ring having 2 to 60 carbon atoms including at least one heteroatom. Unless otherwise stated, the term "heteroatom" used in the present disclosure means N, O, S, P or Si, and the heterocyclic group means a monocycle, ring assemblies, a fused ring system, a spiro compound, etc. including the heteroatom.

Also, the term "heterocyclic group" may include $SO_2$ instead of carbon consisting of cycle. For example, "heterocyclic group" includes compound below.

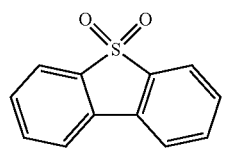

The term "ring" as used herein includes a monocyclic and polycyclic group, a heterocyclic group including at least one heteroatom as well as a hydrocarbon ring, and an aromatic and non-aromatic ring.

The term "polycyclic group" as used herein includes ring assemblies such as biphenyl and terphenyl, a fused ring system and a spiro compound, aromatic and non-aromatic group, and a heterocycle including at least one heteroatom as well as a hydrocarbon ring.

The term "ring assemblies" as used herein is obtained by directly connecting two or more rings (monocyclic group or fused ring system) via a direct linkage or a double bond, where the number of the direct connection is less by one than the total number of the rings included in a compound. In the ring assemblies, the same or different ring systems may be directly connected via a direct linkage or a double bond.

The term "fused ring system" as used herein means a fused ring shape sharing at least two atoms and includes a fused shape of at least two hydrocarbon ring systems and a fused shape of at least one heterocycle including at least one heteroatom. The fused ring system may be an aromatic ring, a heteroaromatic ring, an aliphatic ring, or the combination thereof.

The term "spiro compound" as used herein has "spiro union", and the spiro union means a connection of two rings by sharing only one atom. In this case, the atom shared by the two rings is referred to as "spiro atom". According to the number of the spiro atom included in a compound, the compound is referred to as "monospiro-", "dispiro-", or "trispiro-" compound.

In addition, if a compound is named with continuous prefixes, substituents are listed in the order. For example, an arylalkoxy group means an alkoxy group substituted with an aryl group, an alkoxycarbonyl group means a carbonyl group substituted with an alkoxy group, and an arylcarbonylalkenyl group means an alkenyl group substituted with an arylcarbonyl group, where arylcarbonyl group is a carbonyl group substituted with an aryl group.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a C1-C20 alkyl group, a C1-C20 alkoxy group, a C1-C20 alkylamine group, a C1-C20 alkylthiophene group, a C6-C20 aryithiophene group, a C2-C20 alkenyl group, a C2-C20 alkynyl group, a C3-C20 cycloalkyl group, a C6-C60 aryl group, a C6-C20 aryl group, a C6-C20 aryl group substituted by deuterium, a C8-C20 arylalkenyl group, a silane group, a boron group, a germanium group and a C2-C60 heterocyclic group including at least one heteroatom of O, N, S, Si or P.

Unless otherwise stated, the Formulas used in the present invention are as defined in the index definition of the substituent of the following Formula:

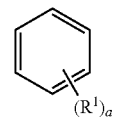

wherein, when a is an integer of zero, the substituent $R^1$ is absent, when a is an integer of 1, the sole substituent $R^1$ is linked to any one of the carbon atoms constituting the benzene ring, when a is an integer of 2 or 3, the substituent $R^1$ s may be the same and different, and are linked as follows: and when a is an integer of 4 to 6, the substituents $R^1$s may be linked to the carbon of the benzene ring in a similar manner, whereas hydrogen atoms linked to carbon constituents of the benzene ring are not represented as usual.

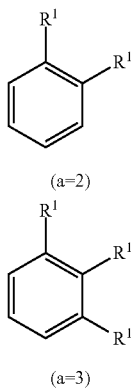

FIG. 1 illustrates an example of an organic electric element according to an embodiment of the present invention.

Referring to FIG. 1, an organic electric element 100 according to the present invention includes a first electrode 120 formed on a substrate 110, a second electrode 180, and an organic material layer between the first electrode 120 and the second electrode 180, which contains the compound according to the present invention. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer may include a hole injection layer 130, a hole transport layer 140, a light emitting layer 150, an electron transport layer 160, and an electron injection layer 170 formed in sequence on the first electrode 120. Here, at least one of the layers may further include a hole blocking layer, an electron blocking layer, an emission-auxiliary layer 151, a buffer layer 141, etc., and the electron transport layer 160 and the like may serve as the hole blocking layer.

Although not shown, the organic electric element according to the present invention may further include at least one protective layer or one capping layer formed on at least one of the sides the first and second electrodes, which is a side opposite to the organic material layer.

The organic light emitting diode according to an embodiment of the present invention may be manufactured using various deposition methods. The organic light emitting diode according to an embodiment of the present invention may be manufactured using a PVD (physical vapor deposition) method or CVD (chemical vapor deposition) method. For example, the organic light emitting diode may be manufactured by depositing a metal, a conductive metal oxide, or a mixture thereof on the substrate 110 to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon. Also, the emission-auxiliary layer 151 may be further formed between the hole transport layer 140 and the light emitting layer 150.

Also, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer etc. Since the organic material layer according to the present invention may be formed in various ways, the scope of protection of the present invention is not limited by a method of forming the organic material layer.

The organic electric element according to the present invention may be of a top emission type, a bottom emission type, or a dual emission type according to the material used. A WOLED (White Organic Light Emitting Device) readily allows for the formation of ultra-high definition images, and is of excellent processability as well as enjoying the advantage of being produced using conventional color filter technologies for LCDs. In this regard, various structures for WOLEDs, used as back light units, have been, in the most part, suggested and patented. Representative among the structures are a parallel side-by-side arrangement of R (Red), G (Green), B (Blue) light-emitting units, a vertical stack arrangement of RGB light-emitting units, and a CCM (color conversion material) structure in which electroluminescence from a blue (B) organic light emitting layer, and photo-luminescence from an inorganic luminescent using the electroluminescence are combined. The present invention is applicable to these WOLEDs.

Further, the organic electric element according to the present invention may be any one of an organic light emitting diode (OLED), an organic solar cell, an organic photo conductor (OPC), an organic transistor (organic TFT), and an element for monochromatic or white illumination.

Another embodiment of the present invention may include an electronic device including a display device, which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, a compound according to an aspect of the present invention will be described.

The compound according to an aspect of the present invention is represented by the following Formula 1 below.

Formula 1

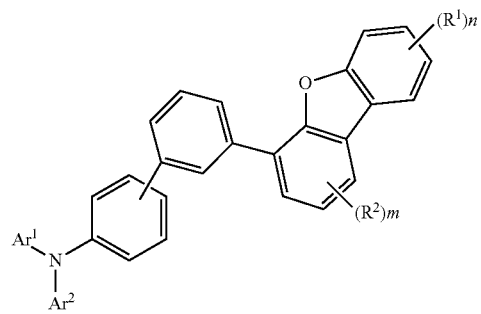

{In the Formula (1) above,
1) n is an integer of 0 to 4, m is an integer of 0 to 3, $R^{1, 2}$ are each independently selected from the group consisting of deuterium; halogen; a C6-C60 aryl group; a fluorenyl group;

a C2-C60 heterocyclic group including at least one heteroatom of O, N, S, Si or P; a fused ring group of a C3-C60 aliphatic ring and a C6-C60 aromatic ring; a C1-C50 alkyl group; a C2-C20 alkenyl group; a C2-C20 alkynyl group; a C1-C30 alkoxy group; a C6-C30 aryloxy group; and -L'-N(R$_a$)(R$_b$) (where L' above may be selected from the group consisting of a single bond; a C6-C60 arylene group; a fluorenylene group; a fused ring group of a C3-C60 aliphatic ring and a C6-060 aromatic ring; and a C2-C60 heterocyclic group, R$_a$ and R$_b$ above are each independently selected from the group consisting of a C6-C60 aryl group; a fluorenyl group; a fused ring group of a C3-C60 aliphatic ring and a C6-C60 aromatic ring; and a C2-C60 heterocyclic group including at least one heteroatom of O, N, S, Si or P), or in the case where m and n are 2 or more, m and n are each in plural and the same or different, and a plurality of R$^1$ or a plurality of R$^2$ may combine to each other to form a ring, and 2) Ar$^{1, 2}$ are a C12-20 aryl group substituted or unsubstituted with deuterium.

Specially, according to the present invention, the compound represented by Formula 1 above provides a compound of Formula 2 below.

Formula 2

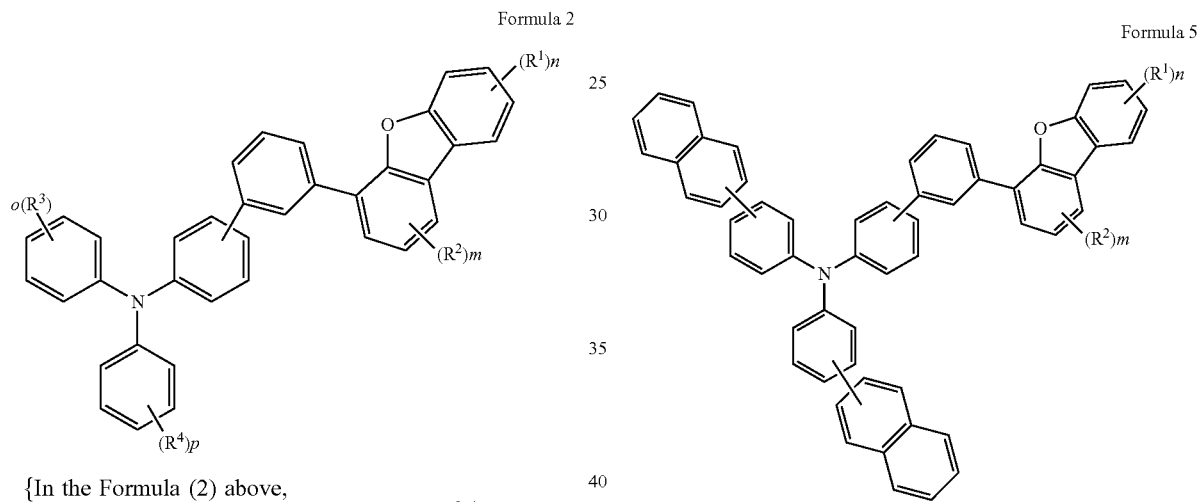

{In the Formula (2) above,
1) o and p are an integer of 1 to 5, and R$^{3,4}$ are each independently a C6-C10 aryl group substituted or unsubstituted with deuterium.
2) R$^{1-2}$, m and n are as defined in Formula 1 above.}

In an aspect of the present invention, the compound represented by Formula 1 above provides any one of compounds of Formula 3 to Formula 5 below.

Formula 3

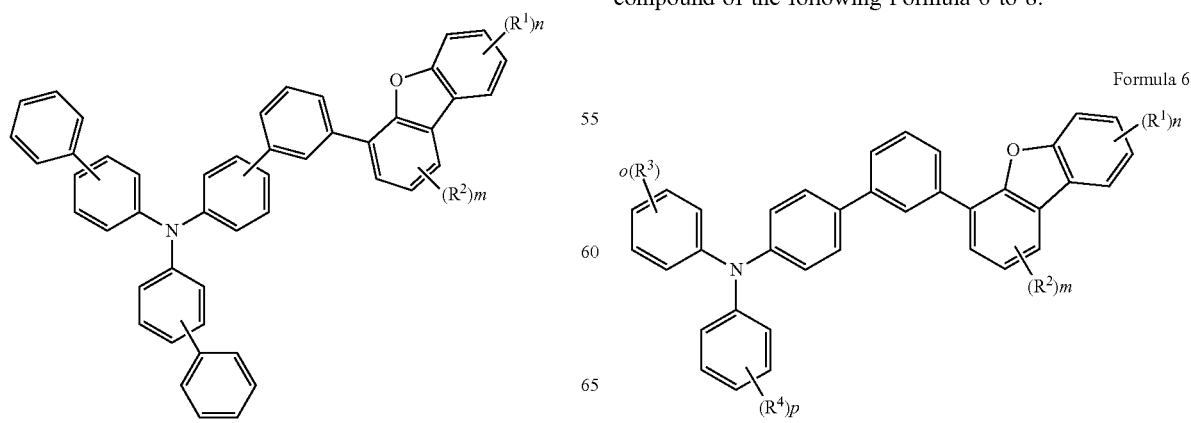

Formula 4

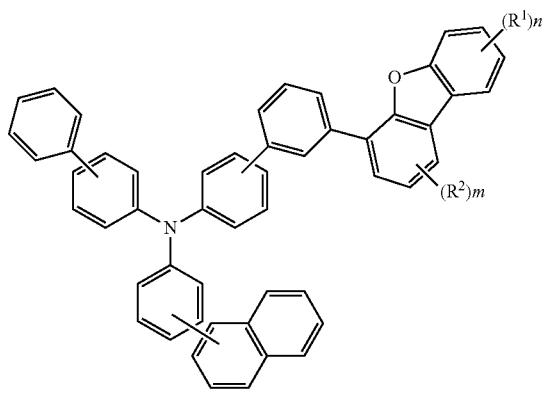

Formula 5

{In Formula 3 to Formula 5 above, R$^{1-2}$, m and n are as defined in Formula 1 above.}

In addition, according to the present invention, the compound represented by the Formula 1 above provides a compound of the following Formula 6 to 8.

Formula 6

Formula 7
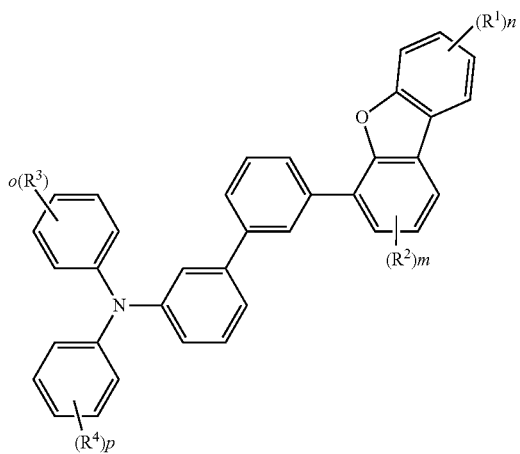
Formula 8
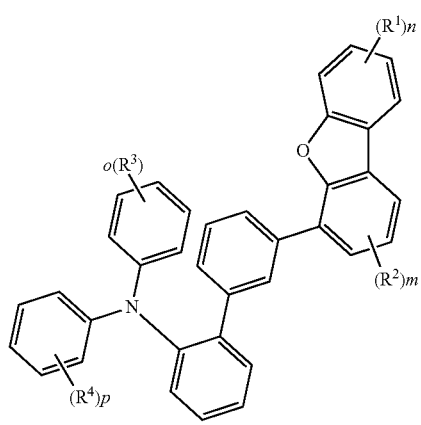
In Formula 6 to Formula 8 above, $R^{1-4}$, m, n, o and p are as defined above.}
More specially, according to the present invention, the compound represented by Formula 1 above includes compounds below
1-1
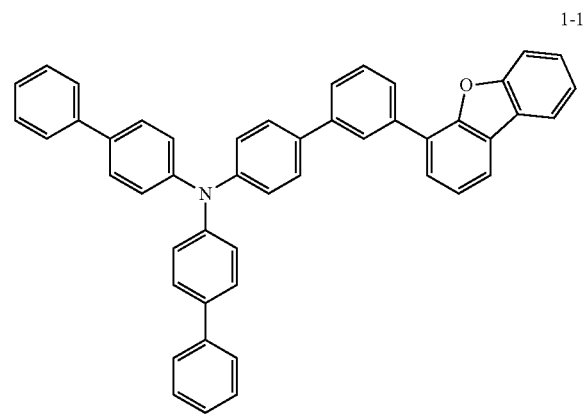
1-2
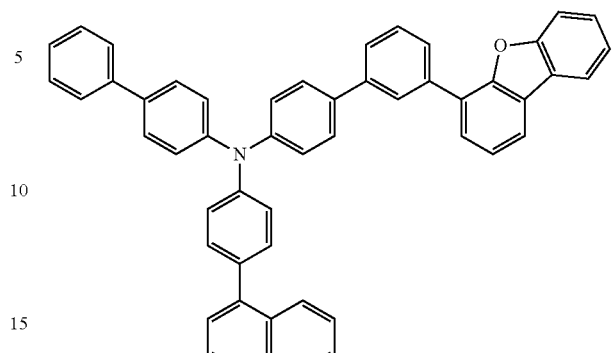
1-3
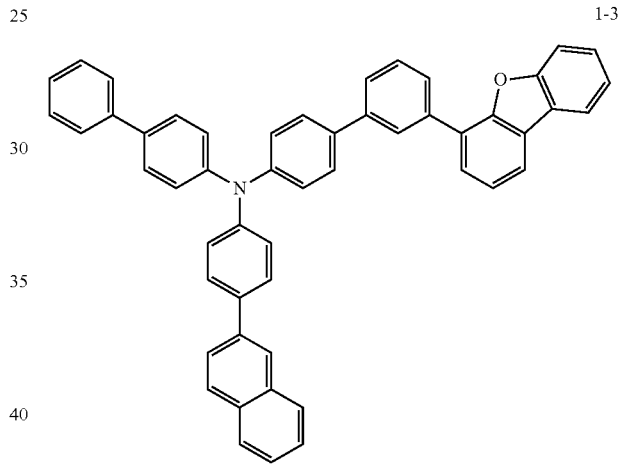
1-4
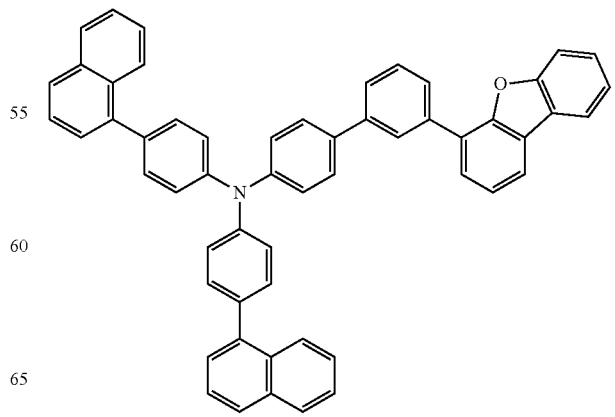

-continued
1-5
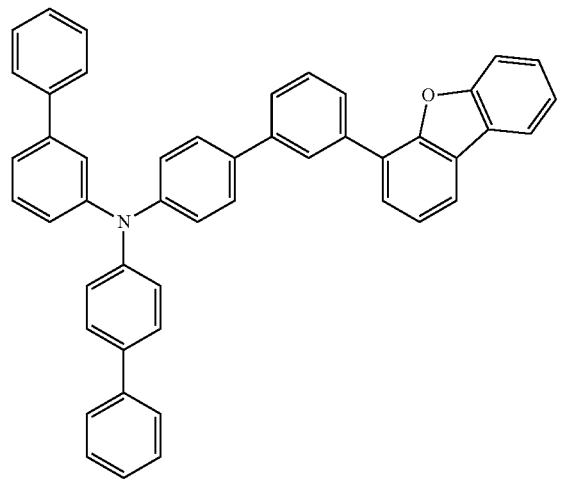
1-6
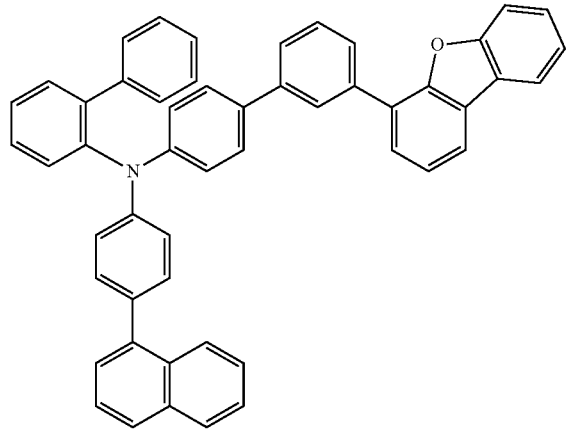
1-7
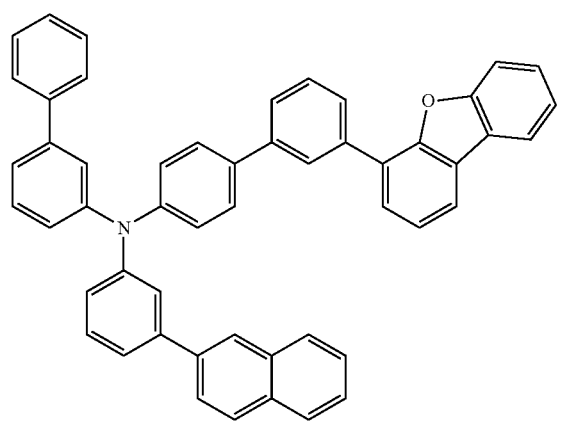
-continued
1-8
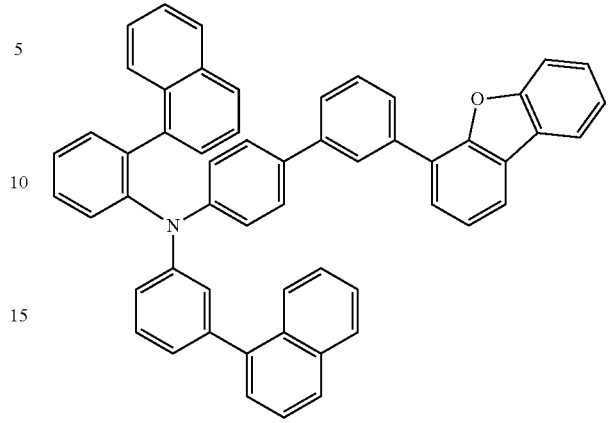
1-9
1-10
1-11
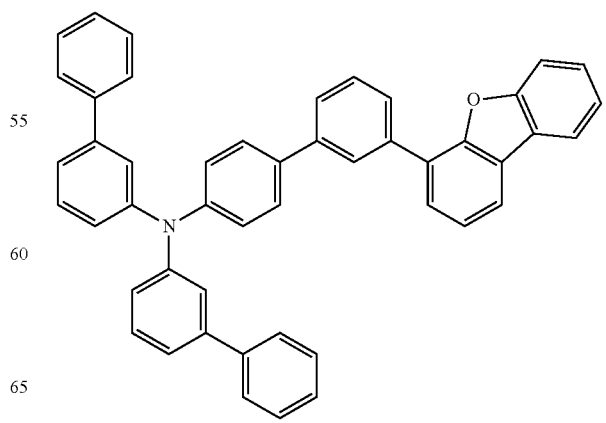

1-12
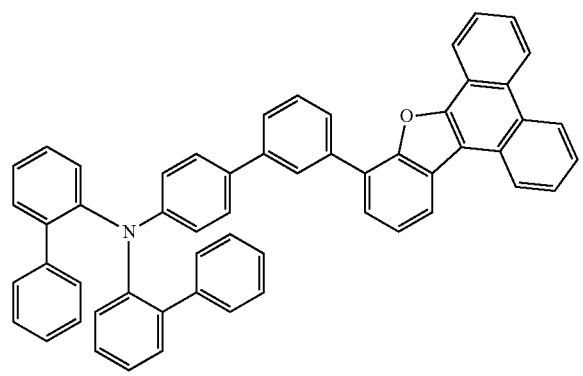
2-4
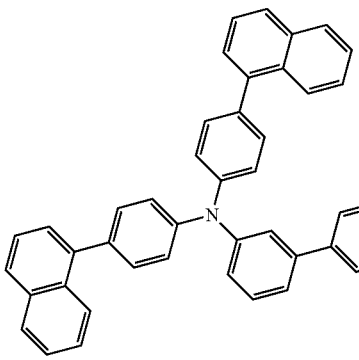
2-1
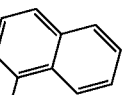
2-5
2-2
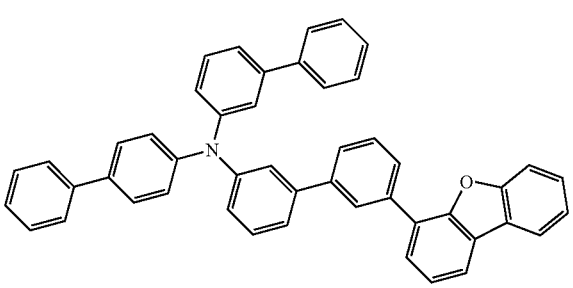
2-6
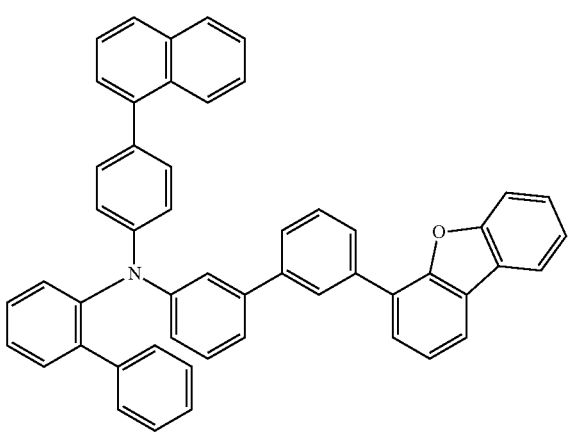
2-3
2-7
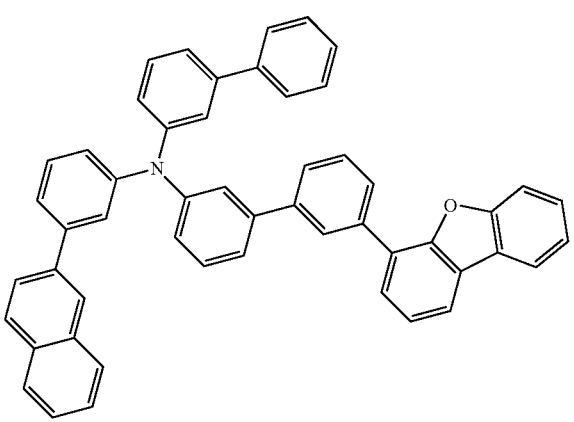

2-8
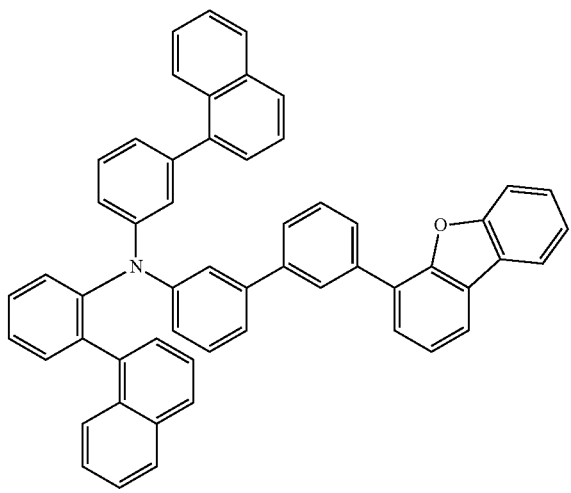
2-9
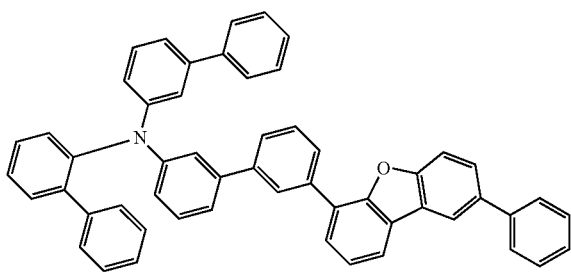
2-10
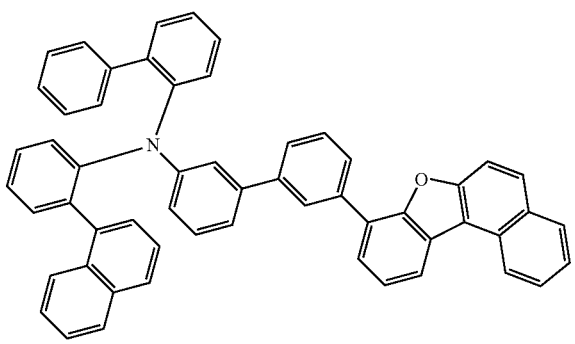
2-11
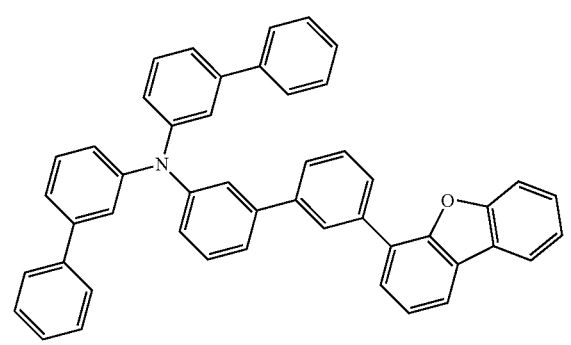
2-12
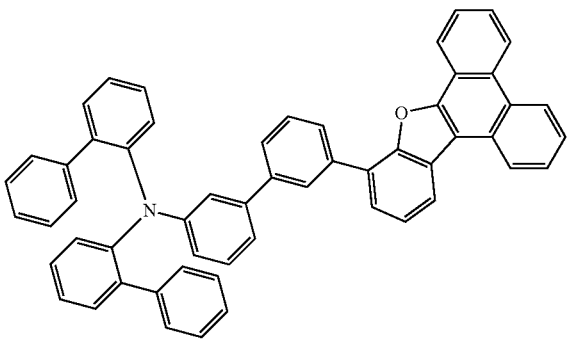
3-1
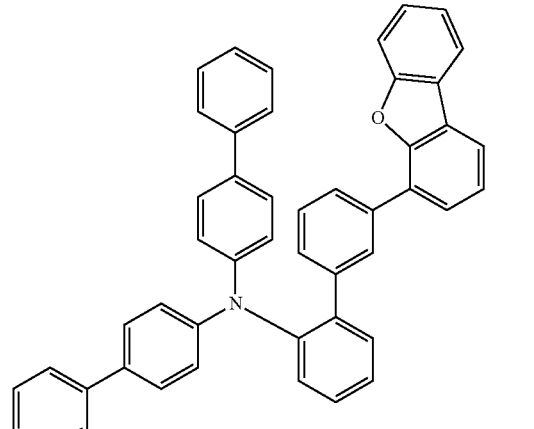
3-2
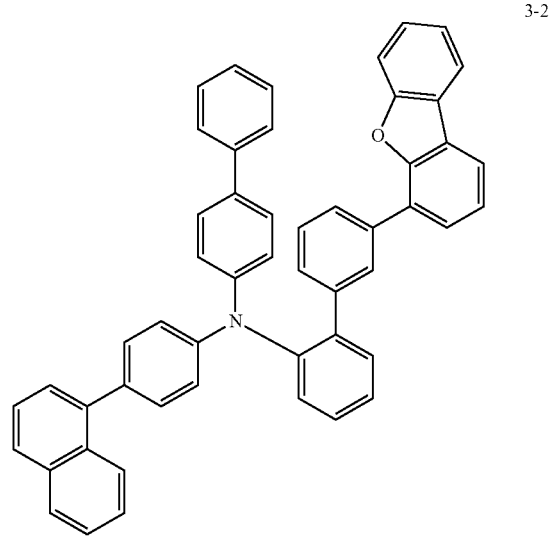

3-3
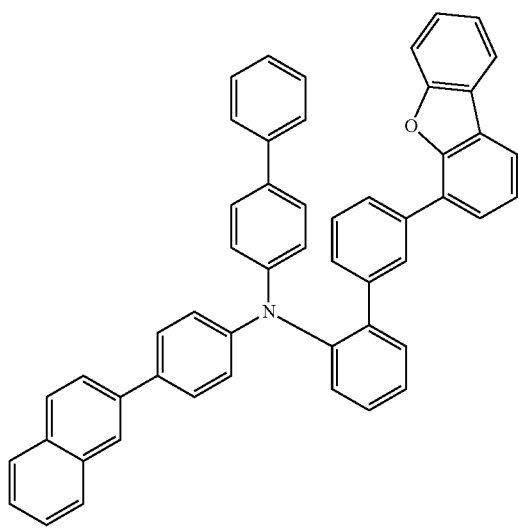
3-4
3-5
3-6
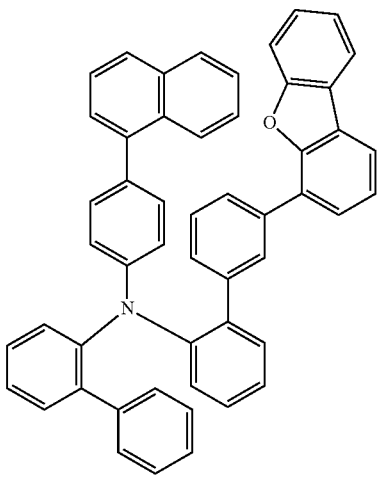
3-7
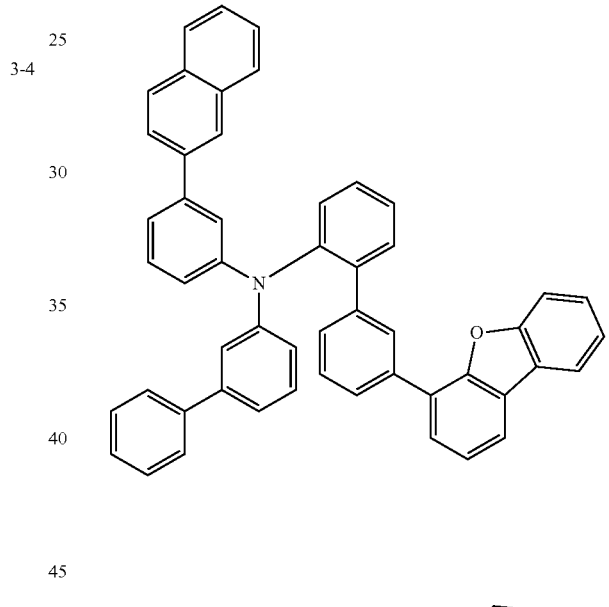
3-8
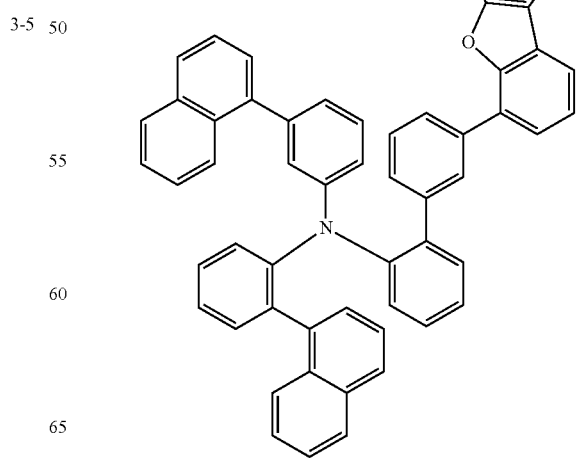

3-9

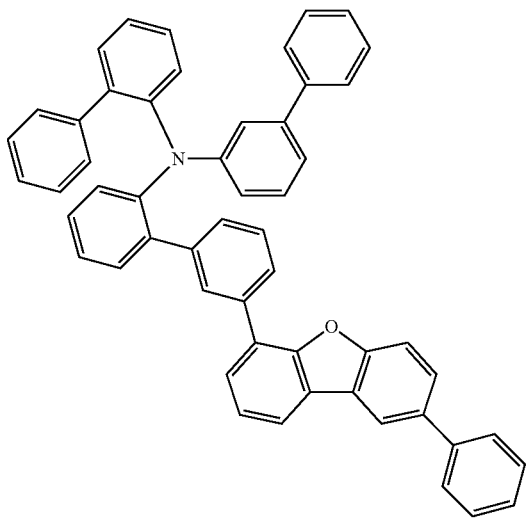

3-10

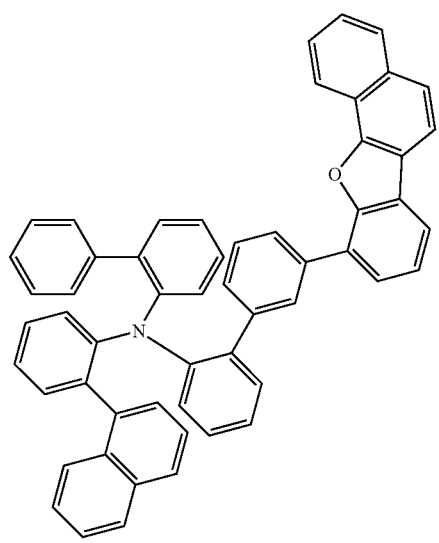

3-11

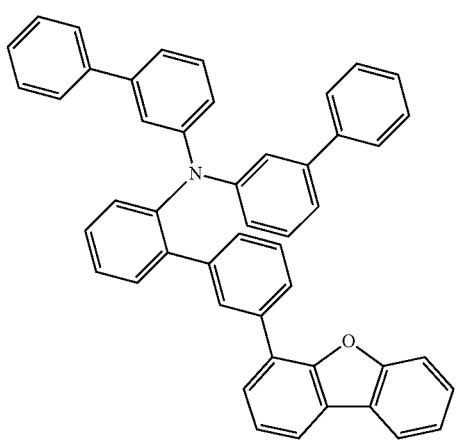

3-12

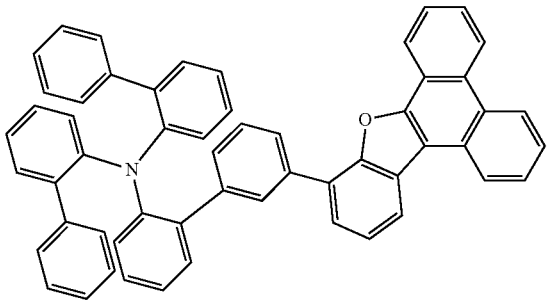

In another aspect of the present invention, there is provided a compound for an organic electric element represented by Formula 1 above In another aspect of the present invention, there is provided an organic electric element comprising the compound represented by Formula 1 above.

The organic electric element can comprise a first electrode, a second electrode, and an organic material layer disposed between the first electrode and the second electrode. The organic material layer can comprise the compound represented by Formula 1. In addition, a light efficiency enhancing layer formed on at least one of the opposite side to the organic layer, or on the opposite side to the organic layer among one side of the second electrode may be further included.

In addition, the present invention provides an organic electric device in which the compound is included in an organic material layer formed between the first electrode and an light emitting layer. The organic layer including the compound forms an EBL, and the compound may be included in the EBL as a mixture of one or two kinds of the compounds.

Further, the organic material layer of the present invention is formed by any one of the spin coating, nozzle printing process, inkjet printing process, slot coating process, dip coating and roll-to-roll process, and the present invention also provides an organic electric element including the compound as the material of the EBL in the organic material layer.

The present invention also provides an electronic device including a display device including the organic electric element; and a control part driving the display apparatus.

According to another aspect, the present invention provides an electronic device characterized in that the organic electric element is at least one of an OLED, an organic solar cell, an organic photo conductor, an organic transistor and an element for monochromic or white illumination. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, Synthesis Examples of the compound represented by Formula according to the present invention and Preparation Examples of an organic electric element will be described in detail by way of example. However, the following examples are only for illustrative purposes and are not intended to limit the scope of the invention.

Synthesis Example

The final product represented by Formula 1 according to the present invention can be synthesized by reaction between Sub 1 and Sub 2 as illustrated in the following Reaction Scheme 1.

<Reaction Scheme 1>

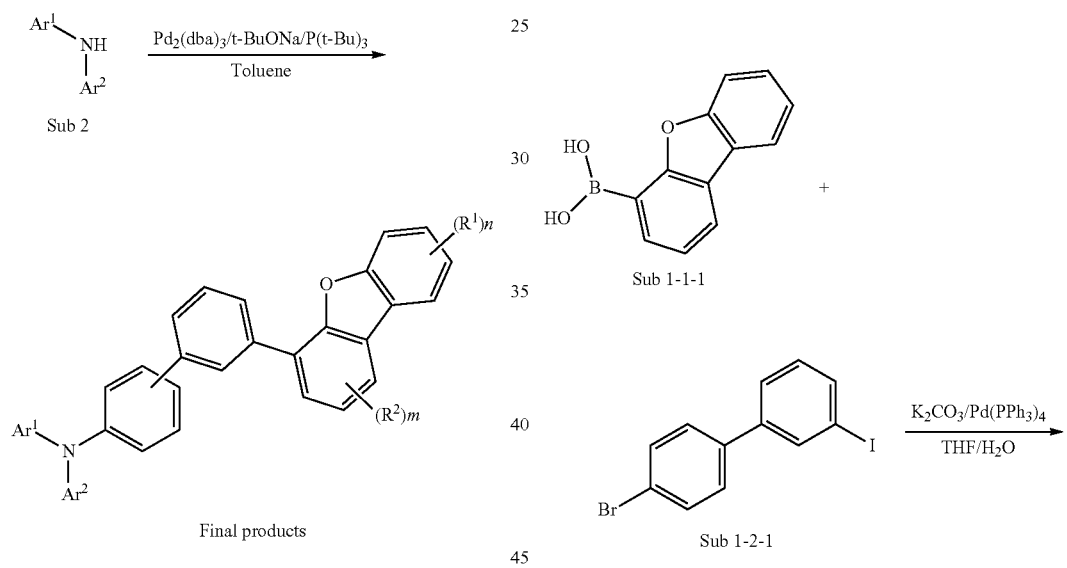

Final products

Synthesis Examples of Sub 1

Sub 1 of Reaction Scheme 1 can be synthesized according to, but not limited to, the reaction path of the following Reaction Scheme 2.

<Reaction Scheme 2>

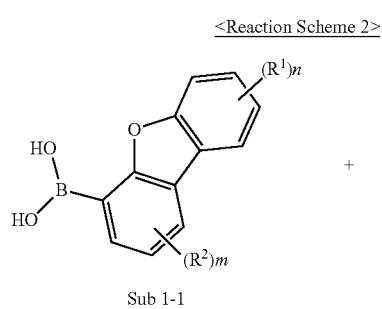

Sub 1-1

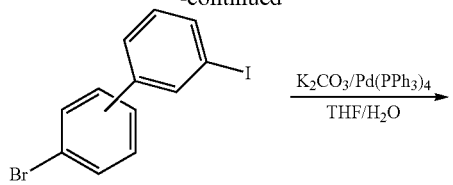

Sub 1-2

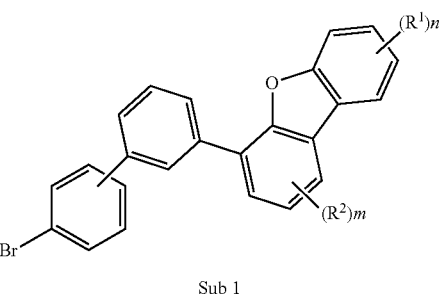

Sub 1

Synthesis Examples of Sub 1(1)

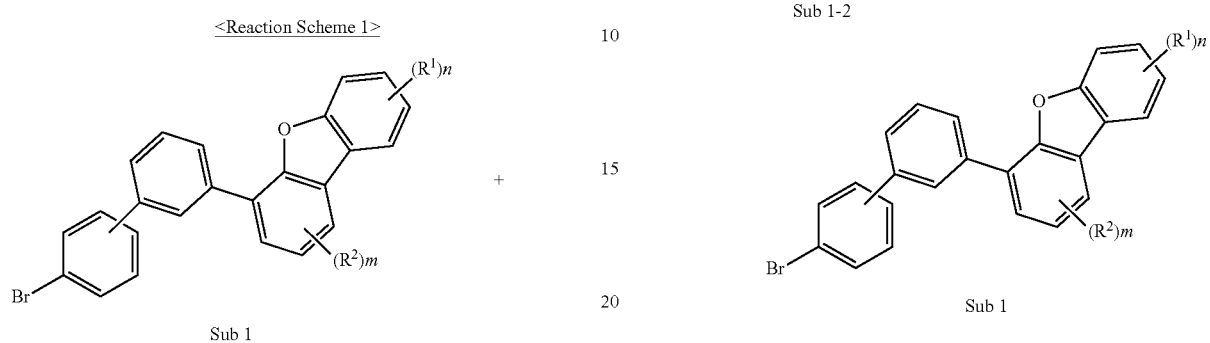

Sub 1-1-1

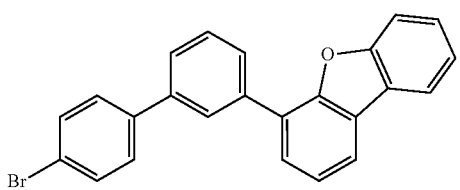

Sub 1-2-1

Sub 1(1)

Sub 1-1-1 (23.3 g, 0.11 mol), 4'-bromo-3-iodo-1,1'-biphenyl (46.7 g, 0.13 mol), $K_2CO_3$ (46.03 g, 0.33 mol), $Pd(PPh_3)_4$ (5.13 g, 4 mol %) were dissolved in anhydrous THF and a small amount of water, followed by reflux at 80° C. for 12 hours. Upon completion of the reaction, the temperature of the reaction product was lowered to room temperature, the reaction product was extracted with $CH_2Cl_2$, and was washed with water. The extracted organic layer was dried with $MgSO_4$ and concentrated, and then the produced organic material was separated by silicgel column to obtain desired Sub1(1) (36.5 g, yield 81%).

Synthesis Examples of Sub 1(2)

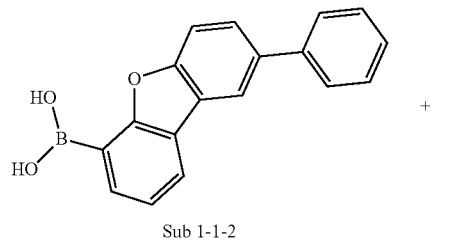
Sub 1-1-2

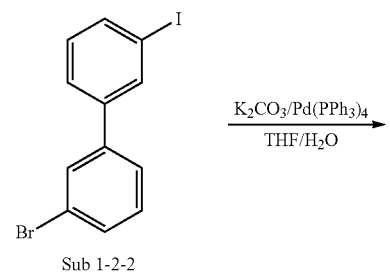
Sub 1-2-2

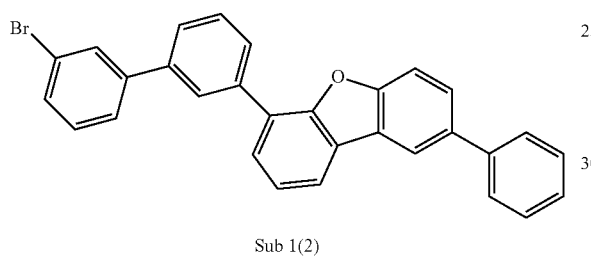
Sub 1(2)

Using Sub 1-1-2 (31.7 g, 0.11 mol), 3-bromo-3'-iodo-1,1'-biphenyl(46.7 g, 0.13 mol) as the starting material, the same procedure as described in the synthesis method of Sub 1(1) above was carried out to obtain desired Sub 1(2) (40.8 g, yield 81%).

Synthesis Examples of Sub 1(3)

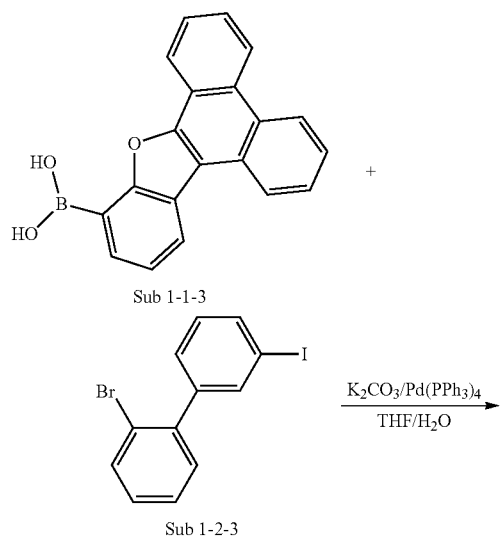
Sub 1-1-3

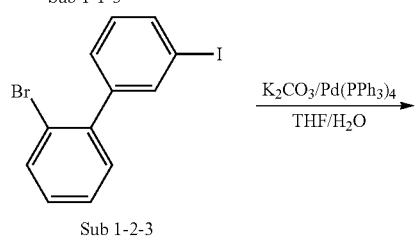
Sub 1-2-3

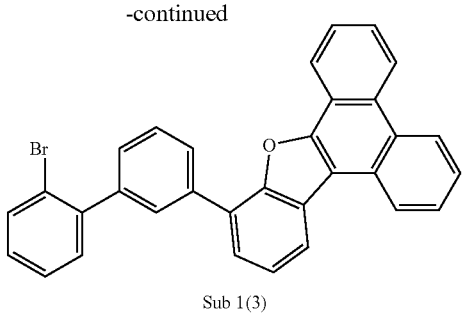
Sub 1(3)

Using Sub 1-1-3 (34.3 g, 0.11 mol), 2-bromo-3'-iodo-1,1'-biphenyl(46.7 g, 0.13 mol) as the starting material, the same procedure as described in the synthesis method of Sub 1(1) above was carried out to obtain desired Sub 1(3) (43.4 g, yield 81%).

The examples of Sub 1 include, but are not limited to, the following compounds.

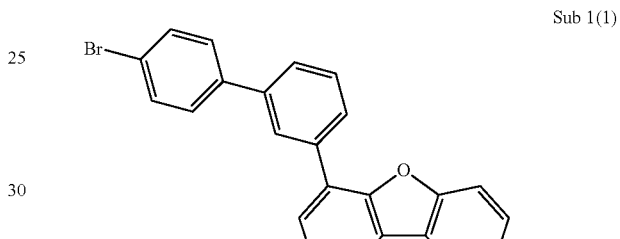
Sub 1(1)

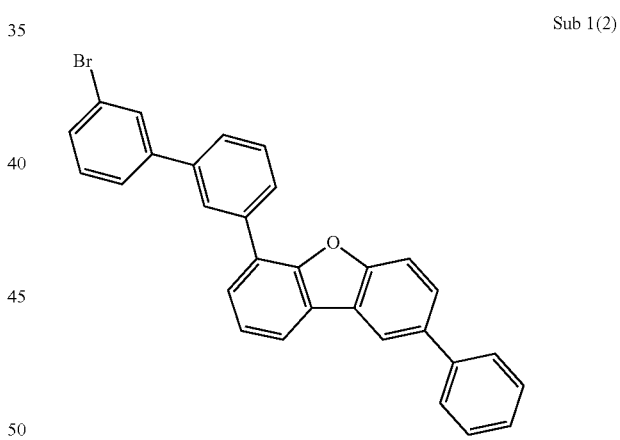
Sub 1(2)

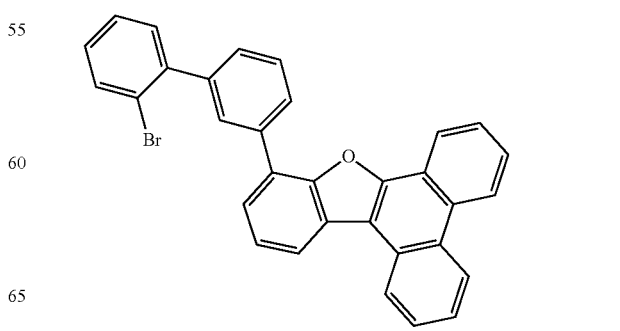
Sub 1(3)

-continued
Sub 1(4)
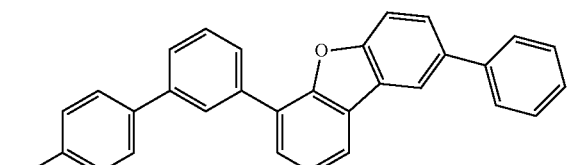
Sub 1(5)
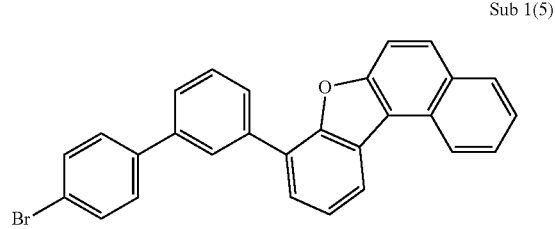
Sub 1(6)
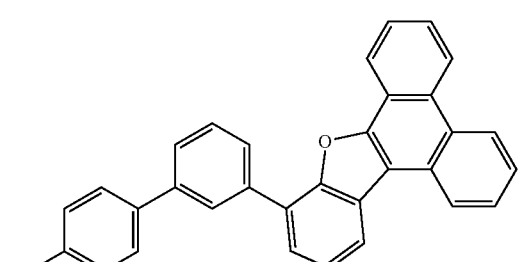
Sub 1(7)
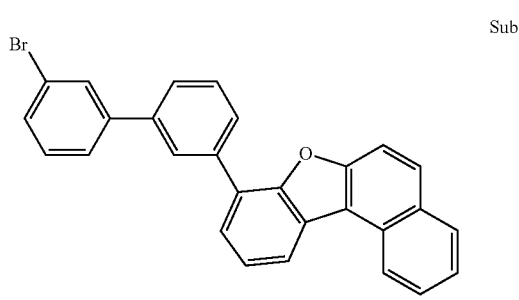
Sub 1(8)
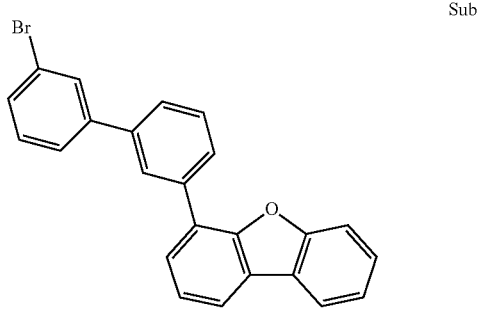
Sub 1(9)
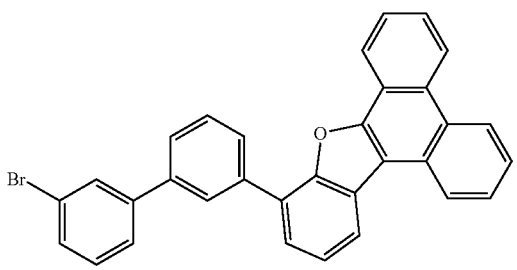
Sub 1(10)
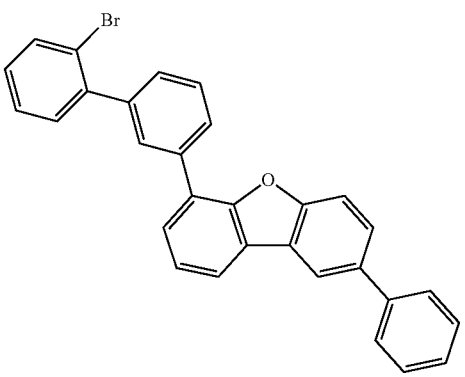
Sub 1(11)
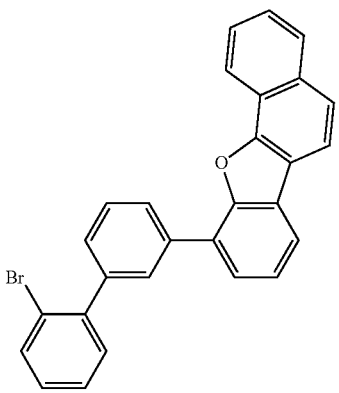
Sub 1(12)
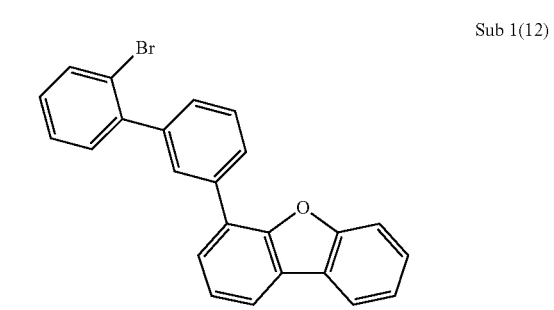

TABLE 1

| compound | FD-MS | compound | FD-MS |
| --- | --- | --- | --- |
| Sub 1(1) | m/z = 398.03($C_{24}H_{15}BrO$ = 399.28) | Sub 1(2) | m/z = 474.06($C_{30}H_{19}BrO$ = 475.38) |
| Sub 1(3) | m/z = 498.06($C_{32}H_{19}BrO$ = 499.40) | Sub 1(4) | m/z = 474.06($C_{30}H_{19}BrO$ = 475.38) |
| Sub 1(5) | m/z = 448.05($C_{28}H_{17}BrO$ = 449.34) | Sub 1(6) | m/z = 498.06($C_{32}H_{19}BrO$ = 499.40) |
| Sub 1(7) | m/z = 448.05($C_{28}H_{17}BrO$ = 449.34) | Sub 1(8) | m/z = 398.03($C_{24}H_{15}BrO$ = 399.28) |
| Sub 1(9) | m/z = 498.06($C_{32}H_{19}BrO$ = 499.40) | Sub 1(10) | m/z = 474.06($C_{30}H_{19}BrO$ = 475.38) |
| Sub 1(11) | m/z = 448.05($C_{28}H_{17}BrO$ = 449.34) | Sub 1(12) | m/z = 398.03($C_{24}H_{15}BrO$ = 399.28) |

Synthesis Examples of Sub 2

Sub 2 of Reaction Scheme 1 can be synthesized according to, but not limited to, the reaction path of the following Reaction Scheme 2.

<Reaction Scheme 2>

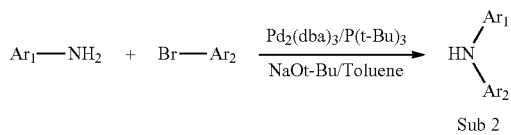

Synthesis Examples of Sub 2(1)

After 4-bromo-1,1'-biphenyl (5.6 g, 24 mmol) was dissolved in toluene, followed by being added [1,1'-biphenyl]-4-amine (3.4 g, 20 mmol), $Pd_2(dba)_3$ (0.5 g, 0.6 mmol), $P(t-Bu)_3$ (0.2 g, 2 mmol), NaOt-Bu (5.8 g, 60 mmol), toluene (300 mL), followed by reflux at 100° C. for 24 hours. Upon completion of the reaction, the reaction product was extracted with ether and water. The organic layer was dried with $MgSO_4$ and concentrated, and then the produced organic material was purified by silicagel column and recrystallized to obtain desired Sub 2(1) 6.2 g, (yield 80%).

The examples of Sub 2 include, but not limited to, the following compounds.

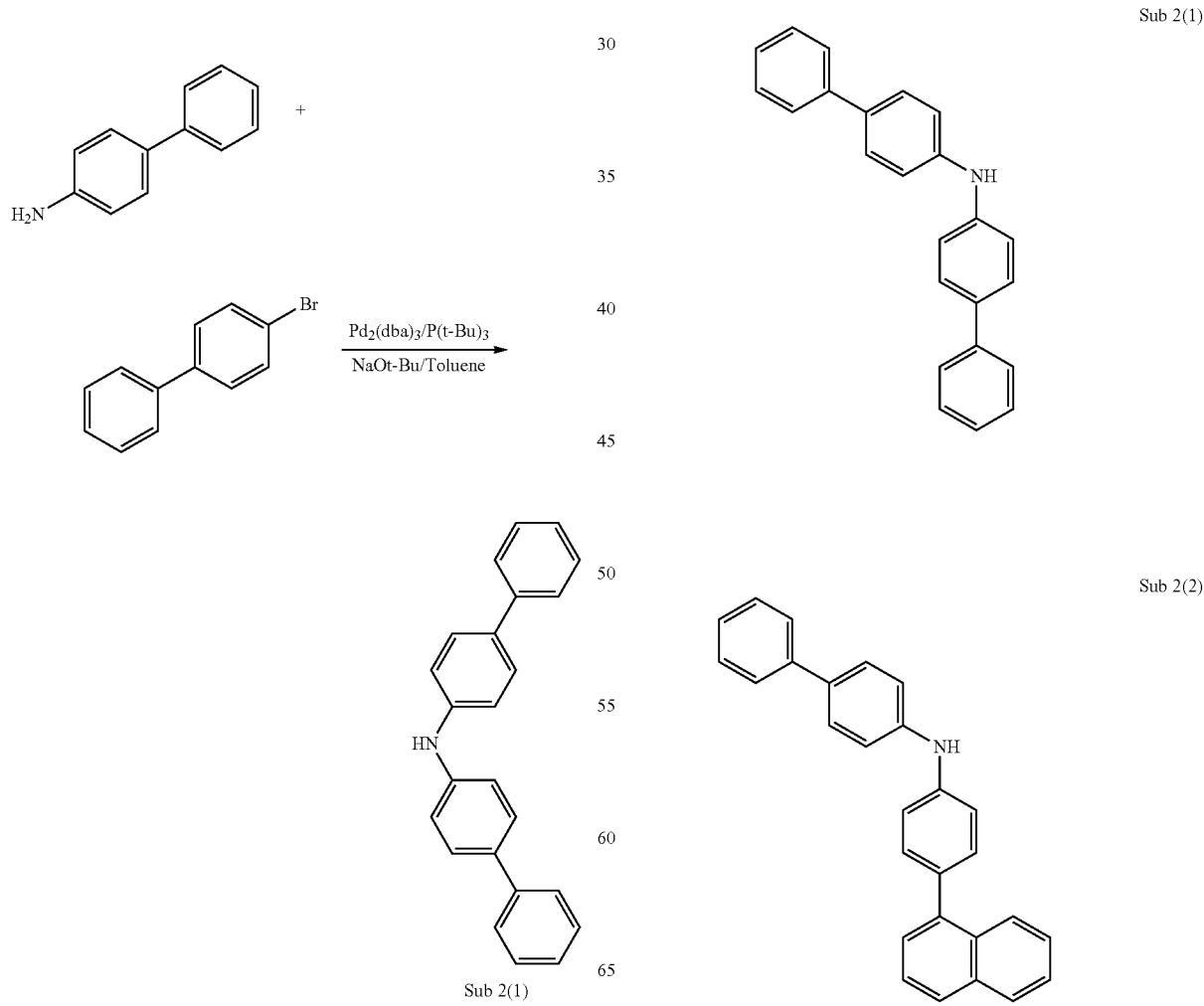

Sub 2(3)
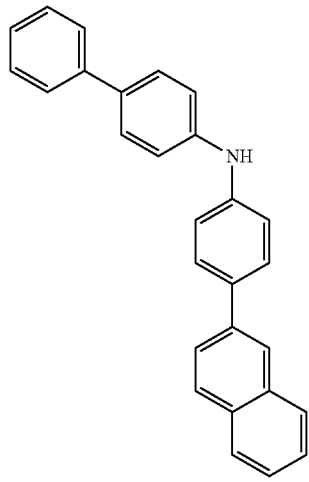
Sub 2(4)
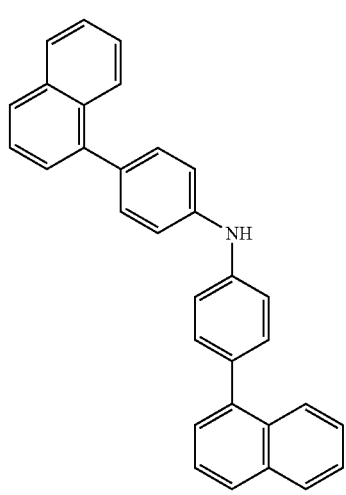
Sub 2(5)
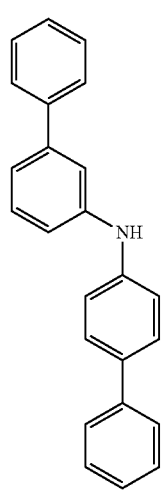
Sub 2(6)
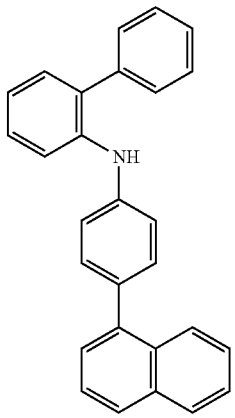
Sub 2(7)
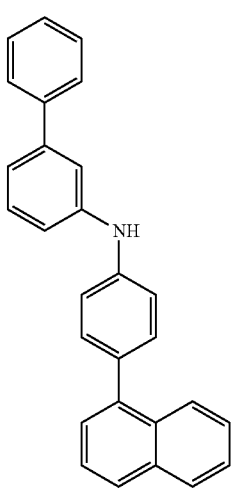
Sub 2(8)
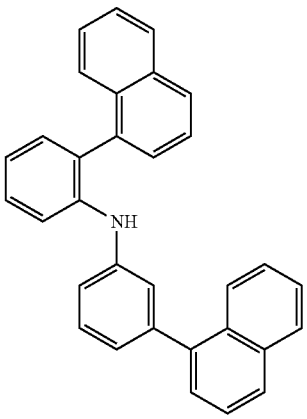

Sub 2(9)
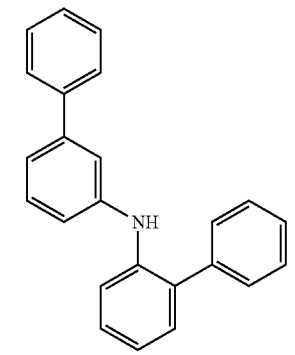
Sub 2(10)
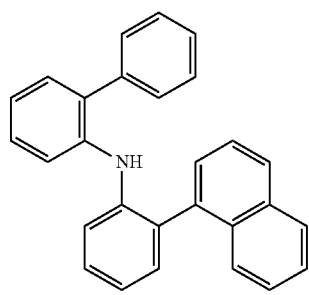
Sub 2(11)
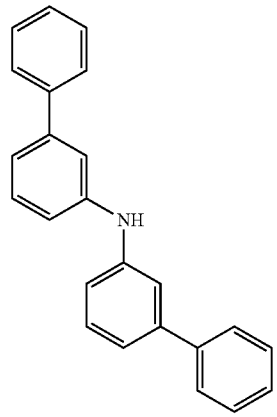
Sub 2(12)
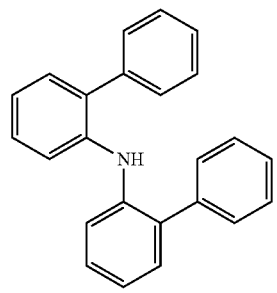
TABLE 2
| compound | FD-MS | compound | FD-MS |
|---|---|---|---|
| Sub 2(1) | m/z = 321.15($C_{24}H_{19}N$ = 321.41) | Sub 2(2) | m/z = 371.17($C_{28}H_{21}N$ = 371.47) |
| Sub 2(3) | m/z = 371.17($C_{28}H_{21}N$ = 371.47) | Sub 2(4) | m/z = 421.18($C_{32}H_{23}N$ = 421.53) |
| Sub 2(5) | m/z = 321.15($C_{24}H_{19}N$ = 321.41) | Sub 2(6) | m/z = 371.17($C_{28}H_{21}N$ = 371.47) |
| Sub 2(7) | m/z = 371.17($C_{28}H_{21}N$ = 371.47) | Sub 2(8) | m/z = 421.18($C_{32}H_{23}N$ = 421.53) |
| Sub 2(9) | m/z = 321.15($C_{24}H_{19}N$ = 321.41) | Sub 2(10) | m/z = 371.17($C_{28}H_{21}N$ = 371.47) |
| Sub 2(11) | m/z = 321.15($C_{24}H_{19}N$ = 321.41) | Sub 2(12) | m/z = 321.15($C_{24}H_{19}N$ = 321.41) |
Synthesis Examples of Final Products
Synthesis Examples of 1-1
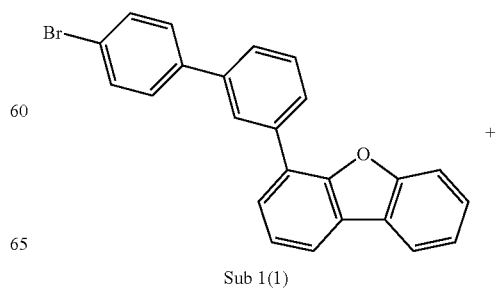
Sub 1(1)

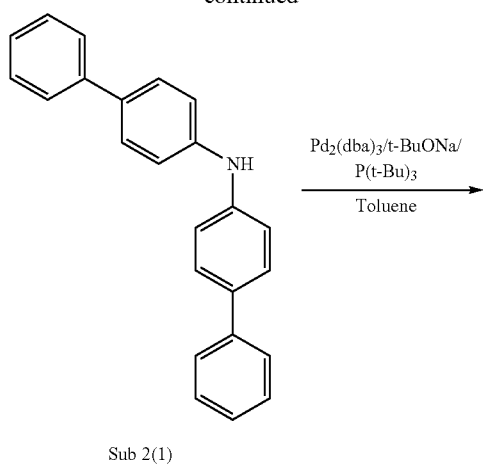

Sub 2(1)

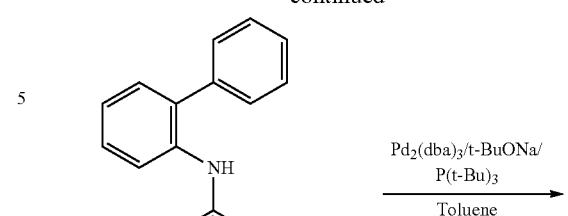

Sub 2(6)

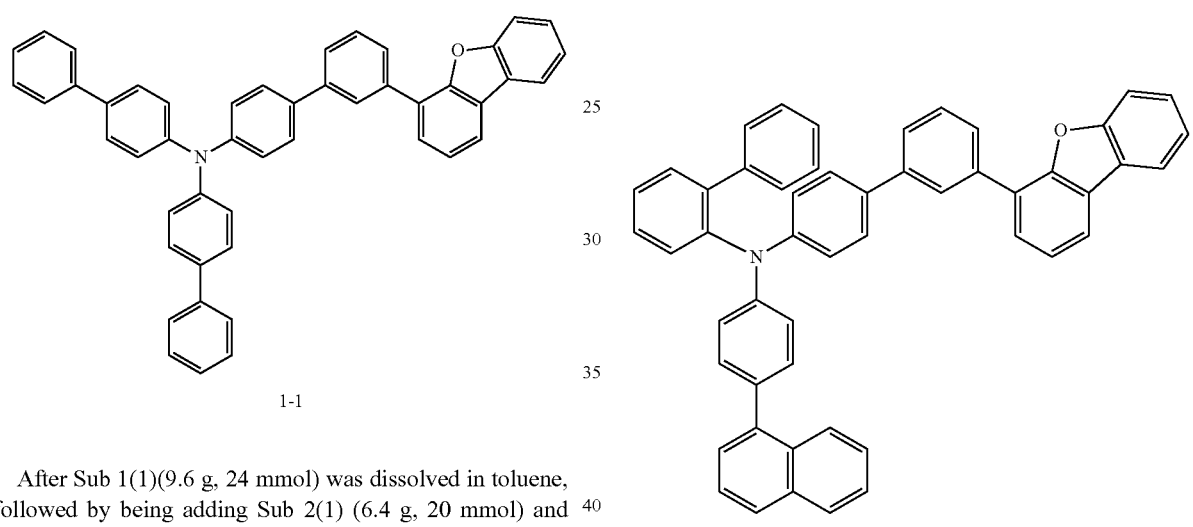

1-1

1-6

After Sub 1(1)(9.6 g, 24 mmol) was dissolved in toluene, followed by being adding Sub 2(1) (6.4 g, 20 mmol) and added with Pd$_2$(dba)$_3$ (0.5 g, 0.6 mmol), P(t-Bu)$_3$ (0.2 g, 2 mmol), NaOt-Bu (5.8 g, 60 mmol), toluene (300 mL), followed by reflux at 100° C. for 24 hours. After the reaction was completed, the reaction product was extracted with ether and water. The organic layer was dried with MgSO$_4$ and concentrated. Then, the produced organic layer was purified by silicagel column and recrystallized to obtain a final compound 13.1 g (yield 85%).

After Sub 1(1)(9.6 g, 24 mmol) was dissolved in toluene, followed by adding Sub 2(6) (7.4 g, 20 mmol), the same procedure as described in Synthesis Method of 1-1 was carried out to obtain desired final compound 13.1 g (yield 79%)

Synthesis Examples of 1-6

Synthesis Examples of 1-11

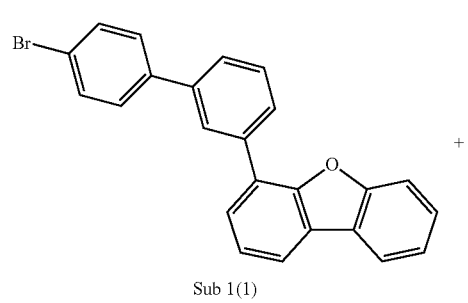

Sub 1(1)

+

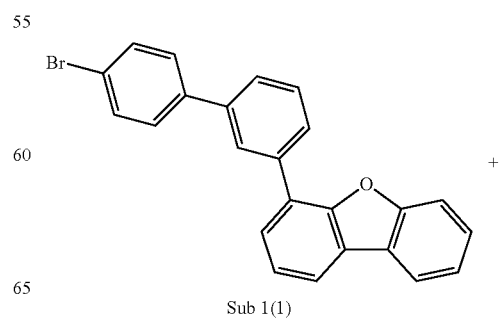

Sub 1(1)

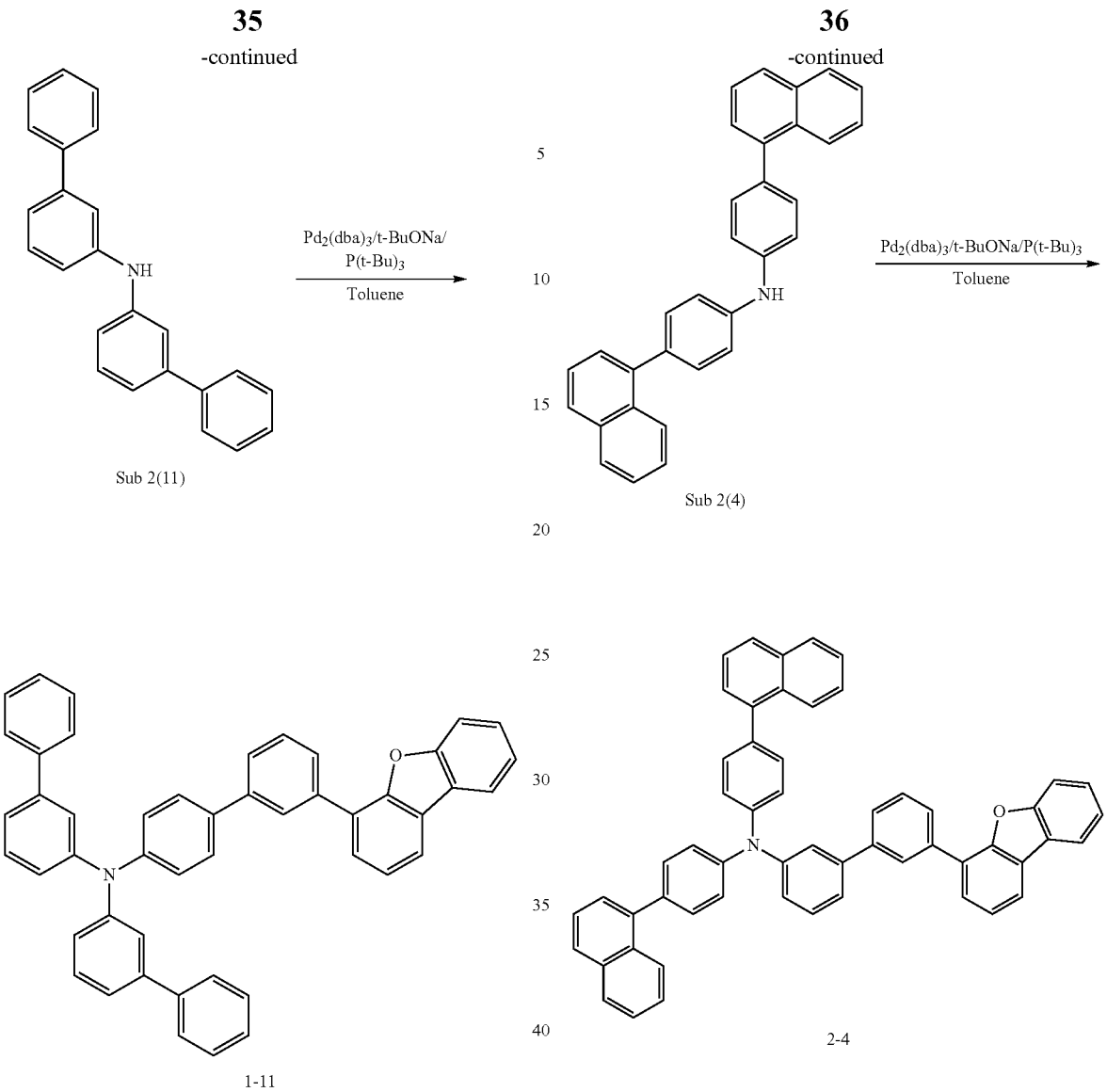

After Sub 1(1)(9.6 g, 24 mmol) was dissolved in toluene, followed by adding Sub 2(11) (6.4 g, 20 mmol), the same procedure as described in Synthesis Method of 1-1 was carried out to obtain desired final compound 12.7 g (yield 83%)

Synthesis Examples of 2-4

After Sub 1(8)(9.6 g, 24 mmol) was dissolved in toluene, followed by adding Sub 2(4) (8.4 g, 20 mmol), the same procedure as described in Synthesis Method of 1-1 was carried out to obtain desired final compound 14.9 g (yield 84%)

Synthesis Examples of 2-5

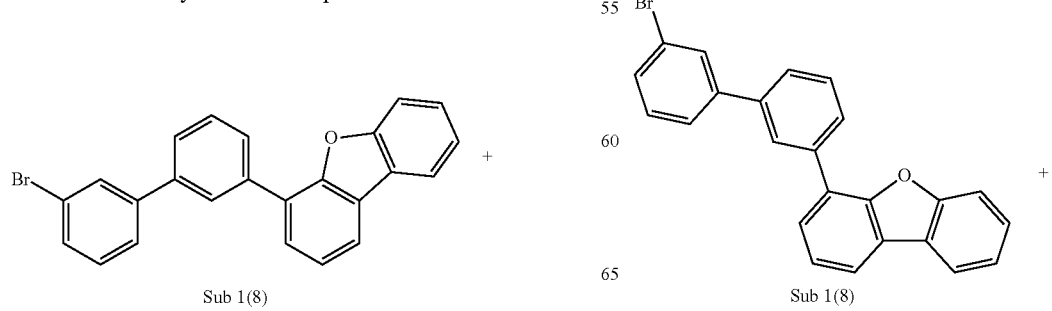

-continued

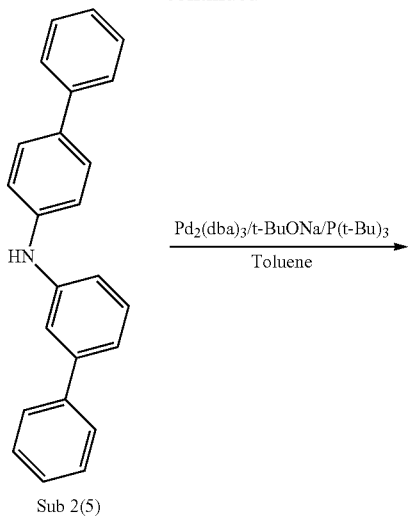

Sub 2(5)

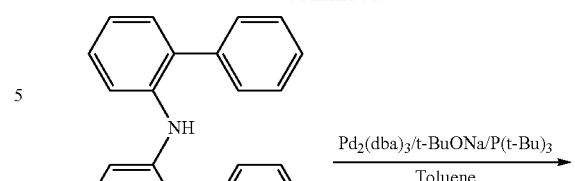

Sub 2(10)

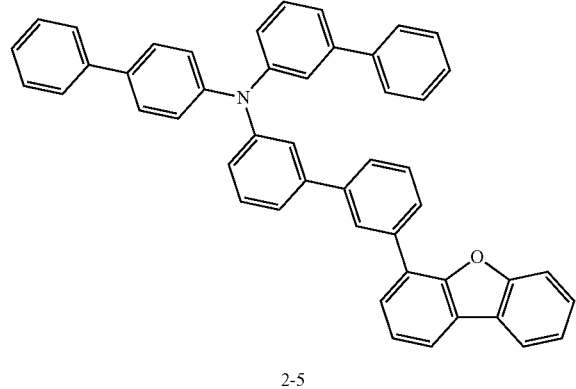

2-10

After Sub 1(7)(10.8 g, 24 mmol) was dissolved in toluene, followed by adding Sub 2(10) (7.4 g, 20 mmol), the same procedure as described in Synthesis Method of 1-1 was carried out to obtain desired final compound 13.9 g (yield 78%)

Synthesis Examples of 3-3

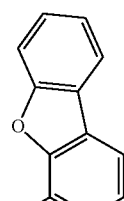

Sub 1(12)

2-5

After Sub 1(8)(9.6 g, 24 mmol) was dissolved in toluene, followed by adding Sub 2(5) (6.4 g, 20 mmol), the same procedure as described in Synthesis Method of 1-1 was carried out to obtain desired final compound 13.2 g (yield 86%)

Synthesis Examples of 2-10

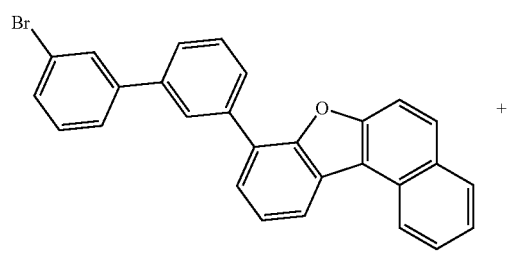

+

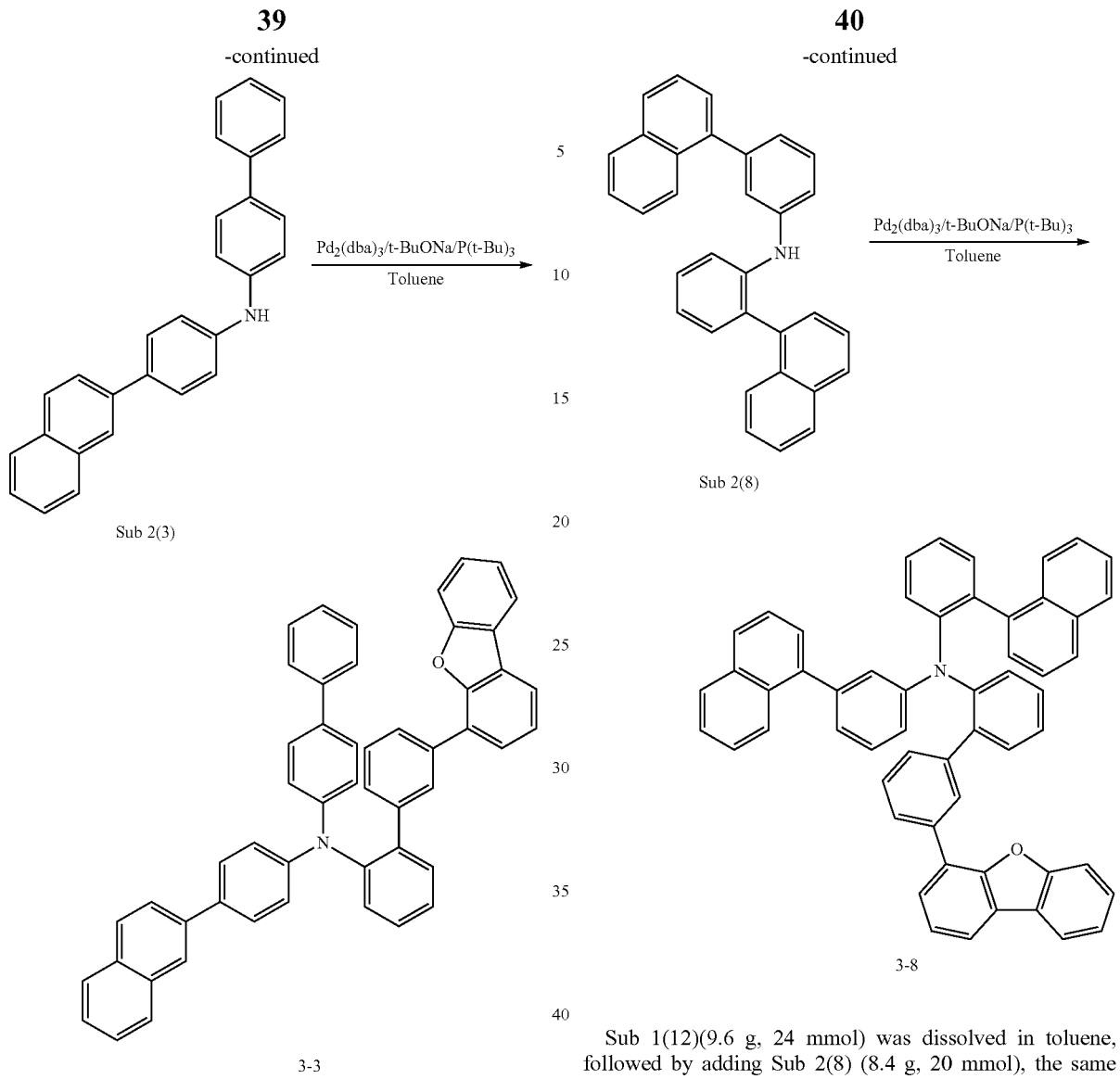

After Sub 1(12)(9.6 g, 24 mmol) was dissolved in toluene, followed by adding Sub 2(3) (7.4 g, 20 mmol), the same procedure as described in Synthesis Method of 1-1 was carried out to obtain desired final compound 12.4 g (yield 75%)

Synthesis Examples of 3-8

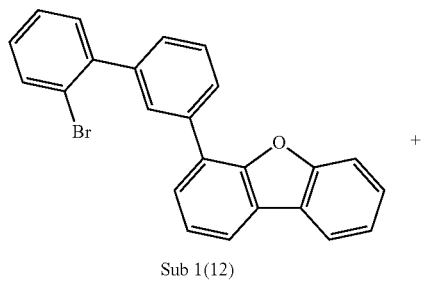

Sub 1(12)(9.6 g, 24 mmol) was dissolved in toluene, followed by adding Sub 2(8) (8.4 g, 20 mmol), the same procedure as described in Synthesis Method of 1-1 was carried out to obtain desired final compound 12.8 g (yield 85%)

Synthesis Examples of 3-9

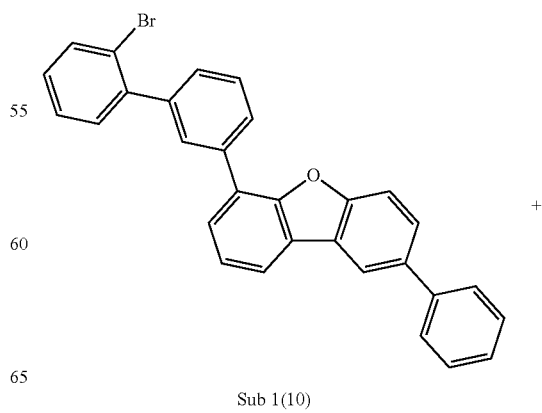

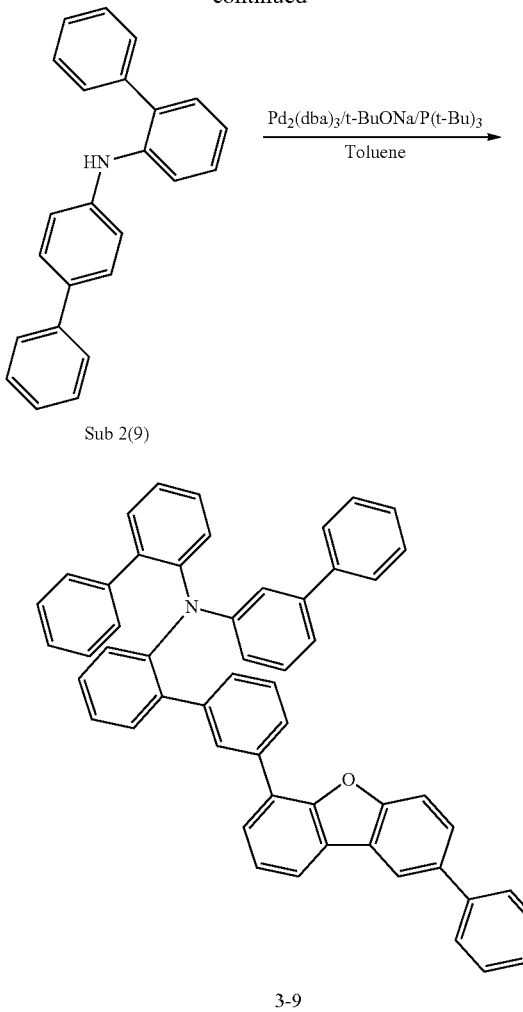

After Sub 1(10)(11.4 g, 24 mmol) was dissolved in toluene, followed by adding Sub 2(9) (6.4 g, 20 mmol), the same procedure as described in Synthesis Method of 1-1 was carried out to obtain desired final compound 13.1 g (yield 76%)

Manufacture and Evaluation of Organic Electric Element

Example 1) Manufacture and Test of Blue OLED (EBL)

On an ITO layer (anode) formed on a glass substrate, 2-TNATA was vacuum deposited to form a hole injection layer with a thickness of 60 nm, and N,N'-bis(1-naphthalenyl)-N,N'-bis-phenyl-(1,1'-biphenyl)-4,4'-diamine (hereinafter will be abbreviated as NPB) was vacuum deposited on the hole injection layer to form a hole transport layer with a thickness of 60 nm. Then, the compound of the present invention was vacuum deposited on the hole transport layer to form an EBL with a thickness of 20 nm. On the EBL, an light emitting layer with a thickness of 30 nm was deposited using 9,10-di(naphthalen-2-yl)anthracene as a host doped with BD-052X (Idemitsukosan) as a dopant in a weight ratio of 96:4. (1,1'-bisphenyl)-4-olato)bis(2-methyl-8-quinolinolato)aluminum (hereinafter will be abbreviated as BAlq) was vacuum deposited to form a hole blocking layer with a thickness of 40 nm, and an electron transport layer was formed using tris(8-quinolinol)aluminum (hereinafter will be abbreviated as Alq3) to a thickness of 40 nm. After that, an alkali metal halide, LiF was deposited as an electron injection layer to a thickness of 0.2 nm, and Al was deposited as a cathode to a thickness of 150 nm to manufacture an OLED.

To the OLEDs which were manufactured in examples and comparative examples, a forward bias direct current voltage was applied, and electroluminescent (EL) properties were measured using PR-650 of Photoresearch Co., and T95 life was measured using a life measuring apparatus manufactured by McScience Inc. with a reference luminance of 500 cd/m². In the following table, the results on the manufacture of a device and evaluation are shown.

Comparative Example 1

Except for not using EBL, an OLED was manufactured in the same manner as described in the embodiment 1 above.

Comparative Example 2 to Comparative Example 3

Except that EBL was formed in using the Comparative Example 1 to 2, an OLED was manufactured in the same manner as described in the embodiment 1 above, instead of the inventive compound.

TABLE 3

| compound | FD-MS | compound | FD-MS |
|---|---|---|---|
| 1-1 | m/z = 639.26($C_{48}H_{33}NO$ = 639.78) | 1-2 | m/z = 689.27($C_{52}H_{35}NO$ = 689.84) |
| 1-3 | m/z = 689.27($C_{52}H_{35}NO$ = 689.84) | 1-4 | m/z = 739.29($C_{56}H_{37}NO$ = 739.90) |
| 1-5 | m/z = 639.26($C_{48}H_{33}NO$ = 639.78) | 1-6 | m/z = 689.27($C_{52}H_{35}NO$ = 689.84) |
| 1-7 | m/z = 689.27($C_{52}H_{35}NO$ = 689.84) | 1-8 | m/z = 739.29($C_{56}H_{37}NO$ = 739.90) |
| 1-9 | m/z = 715.29($C_{54}H_{37}NO$ = 715.88) | 1-10 | m/z = 739.29($C_{56}H_{37}NO$ = 739.90) |
| 1-11 | m/z = 639.26($C_{48}H_{33}NO$ = 639.78) | 1-12 | m/z = 739.29($C_{56}H_{37}NO$ = 739.90) |
| 2-1 | m/z = 639.26($C_{48}H_{33}NO$ = 639.78) | 2-2 | m/z = 689.27($C_{52}H_{35}NO$ = 689.84) |
| 2-3 | m/z = 689.27($C_{52}H_{35}NO$ = 689.84) | 2-4 | m/z = 739.29($C_{56}H_{37}NO$ = 739.90) |
| 2-5 | m/z = 639.26($C_{48}H_{33}NO$ = 639.78) | 2-6 | m/z = 689.27($C_{52}H_{35}NO$ = 689.84) |
| 2-7 | m/z = 689.27($C_{52}H_{35}NO$ = 689.84) | 2-8 | m/z = 739.29($C_{56}H_{37}NO$ = 739.90) |
| 2-9 | m/z = 715.29($C_{54}H_{37}NO$ = 715.88) | 2-10 | m/z = 739.29($C_{56}H_{37}NO$ = 739.90) |
| 2-11 | m/z = 639.26($C_{48}H_{33}NO$ = 639.78) | 2-12 | m/z = 739.29($C_{56}H_{37}NO$ = 739.90) |
| 3-1 | m/z = 639.26($C_{48}H_{33}NO$ = 639.78) | 3-2 | m/z = 689.27($C_{52}H_{35}NO$ = 689.84) |
| 3-3 | m/z = 689.27($C_{52}H_{35}NO$ = 689.84) | 3-4 | m/z = 739.29($C_{56}H_{37}NO$ = 739.90) |
| 3-5 | m/z = 639.26($C_{48}H_{33}NO$ = 639.78) | 3-6 | m/z = 689.27($C_{52}H_{35}NO$ = 689.84) |
| 3-7 | m/z = 689.27($C_{52}H_{35}NO$ = 689.84) | 3-8 | m/z = 739.29($C_{56}H_{37}NO$ = 739.90) |
| 3-9 | m/z = 715.29($C_{54}H_{37}NO$ = 715.88) | 3-10 | m/z = 739.29($C_{56}H_{37}NO$ = 739.90) |
| 3-11 | m/z = 639.26($C_{48}H_{33}NO$ = 639.78) | 3-12 | m/z = 739.29($C_{56}H_{37}NO$ = 739.90) |

Comparative Example 2
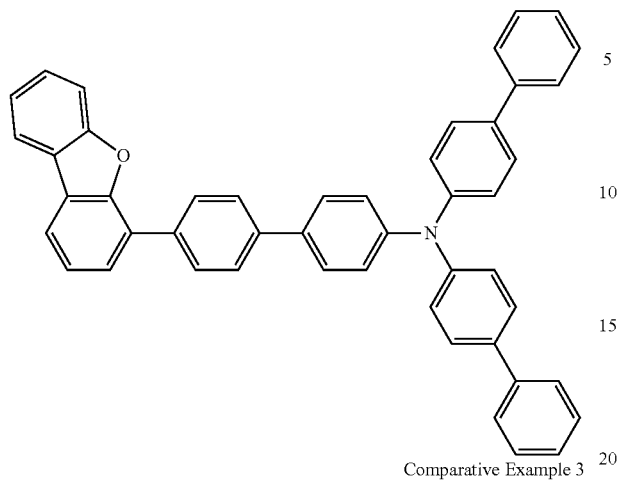
Comparative Example 3
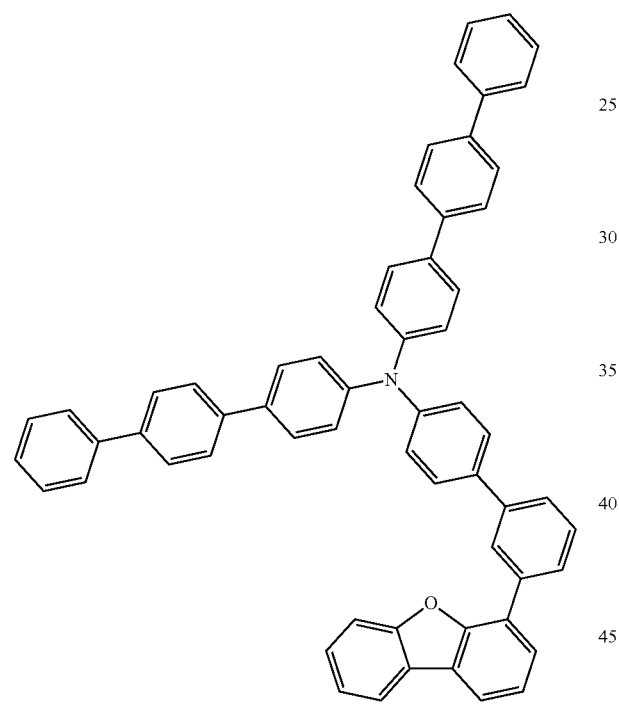
TABLE 4
| | compound | Voltage | Current Density | Brightness (cd/m2) | Efficiency | Lifetime T(95) | CIE (x, y) |
|---|---|---|---|---|---|---|---|
| Comparative example (1) | — | 6.0 | 13.5 | 500.0 | 3.7 | 61.8 | (0.15, 0.13) |
| Comparative example (2) | Comparative compound 1 | 6.1 | 11.1 | 500.0 | 4.5 | 83.5 | (0.14, 0.14) |
| Comparative example (3) | Comparative compound 2 | 5.8 | 9.8 | 500.0 | 5.1 | 95.6 | (0.15, 0.14) |
| Example (1) | compound (1-1) | 5.2 | 7.9 | 500.0 | 6.3 | 111.3 | (0.14, 0.14) |
| Example (2) | compound (1-2) | 5.3 | 7.8 | 500.0 | 6.4 | 111.7 | (0.15, 0.13) |
| Example (3) | compound (1-3) | 5.2 | 7.9 | 500.0 | 6.4 | 111.6 | (0.15, 0.16) |

TABLE 4-continued

| | compound | Voltage | Current Density | Brightness (cd/m2) | Efficiency | Lifetime T(95) | CIE (x, y) |
|---|---|---|---|---|---|---|---|
| Example (4) | compound (1-4) | 5.2 | 7.8 | 500.0 | 6.4 | 110.3 | (0.15, 0.14) |
| example (5) | compound (1-5) | 5.3 | 7.8 | 500.0 | 6.4 | 118.5 | (0.15, 0.13) |
| example (6) | compound (1-6) | 5.3 | 7.9 | 500.0 | 6.4 | 112.6 | (0.14, 0.14) |
| example (7) | compound (1-7) | 5.3 | 7.8 | 500.0 | 6.4 | 118.7 | (0.15, 0.14) |
| example (8) | compound (1-8) | 5.3 | 7.7 | 500.0 | 6.5 | 110.3 | (0.15, 0.13) |
| example (9) | compound (2-1) | 5.3 | 8.1 | 500.0 | 6.2 | 114.5 | (0.15, 0.14) |
| example (10) | compound (2-2) | 5.4 | 8.2 | 500.0 | 6.1 | 114.8 | (0.15, 0.13) |
| example (11) | compound (2-3) | 5.3 | 8.2 | 500.0 | 6.1 | 119.6 | (0.14, 0.14) |
| example (12) | compound (2-4) | 5.4 | 8.3 | 500.0 | 6.0 | 113.8 | (0.14, 0.14) |
| example (13) | compound (2-5) | 5.3 | 8.2 | 500.0 | 6.1 | 117.5 | (0.14, 0.14) |
| example (14) | compound (2-6) | 5.4 | 8.1 | 500.0 | 6.2 | 117.1 | (0.15, 0.13) |
| example (15) | compound (2-7) | 5.4 | 8.1 | 500.0 | 6.2 | 112.6 | (0.15, 0.14) |
| example (16) | compound (2-8) | 5.3 | 8.1 | 500.0 | 6.2 | 114.1 | (0.15, 0.14) |
| example (17) | compound (3-1) | 5.4 | 8.4 | 500.0 | 5.9 | 112.0 | (0.15, 0.13) |
| example (18) | compound (3-2) | 5.5 | 8.6 | 500.0 | 5.8 | 116.9 | (0.15, 0.13) |
| example (19) | compound (3-3) | 5.4 | 8.3 | 500.0 | 6.0 | 112.7 | (0.14, 0.14) |
| example (20) | compound (3-4) | 5.4 | 8.5 | 500.0 | 5.9 | 113.3 | (0.15, 0.14) |
| example (21) | compound (3-5) | 5.4 | 8.5 | 500.0 | 5.9 | 113.5 | (0.15, 0.14) |
| example (22) | compound (3-6) | 5.4 | 8.5 | 500.0 | 5.9 | 114.8 | (0.14, 0.14) |
| example (23) | compound (3-7) | 5.4 | 8.4 | 500.0 | 6.0 | 119.0 | (0.15, 0.13) |
| example (24) | compound (3-8) | 5.5 | 8.5 | 500.0 | 5.9 | 110.4 | (0.15, 0.16) |

As is apparent from data of Table 4 above, in case that the organic electroluminescent device using the material of the present invention, the main substituent were found to be low driving voltage, significantly high luminous efficiency and high life span, compared to that of not using EBL or that of Comparative Example using Comparative compound 1 and 2.

In other words, the results for Comparative Examples 1 and 2 and Examples 1-24 using the EBL are better when compared to those for Comparative example 1 not using the EBL, and the driving voltage and life of Comparative Compound 2 and the inventive compounds having a non-linear linker are improved, and particularly, efficiency is markedly improved when compared to those for Comparative Compound 1 which is similar to the inventive compounds, however in which, a linker-amine group is linearly substituted at position 4 of dibenzofuran. The results are considered to be obtainable, because Comparative Compound 2 and the inventive compounds having the non-linear linker have a decreased bonding angle than Comparative Compound 1 having a linear linker, and so, has a high T1 value and improved electron blocking ability.

Figure 2:
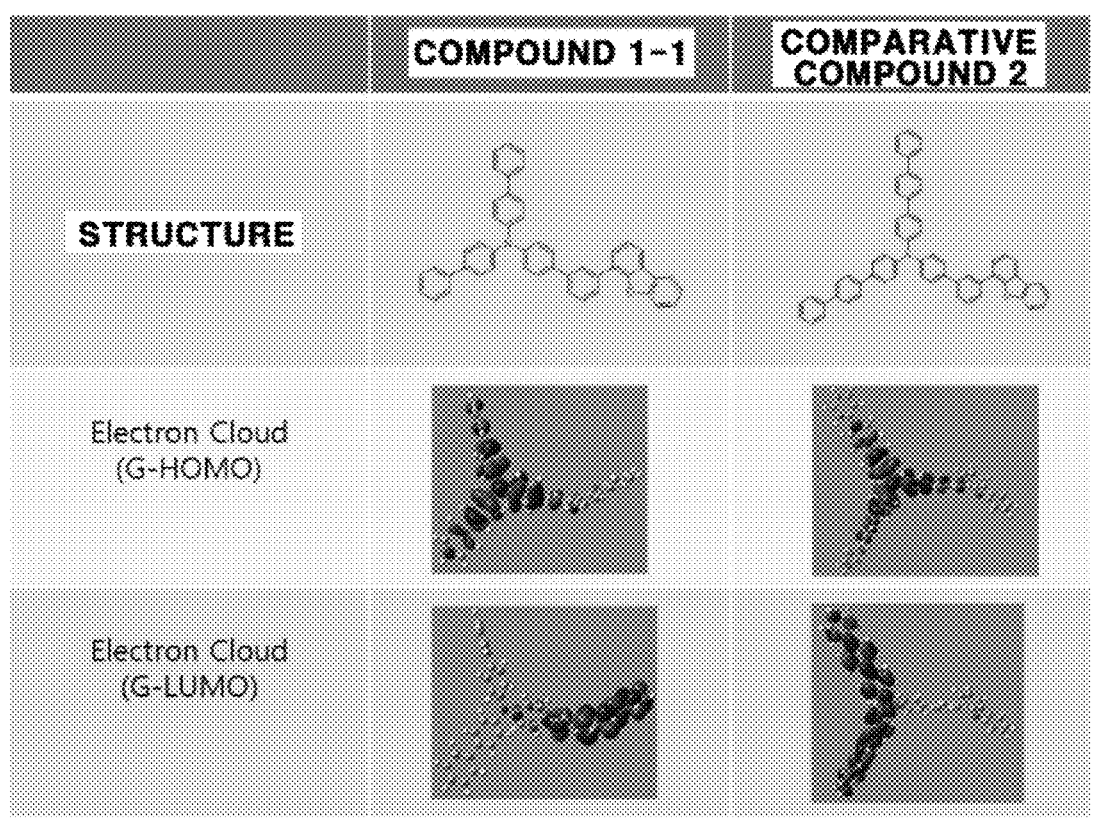
FIG. 2 illustrates a comparison between Compound 1-1 and Comparative Compound 2 in terms of structure, Electron Cloud (G-HOMO) and Electron Cloud (G-LUMO).

When comparing Comparative Compound 2 having the same non-linear linker as the inventive compounds with the inventive compound, it may be confirmed that even though the cores are the same, the physical properties of compounds are markedly changed according to the kind of substituents, as can be seen in FIG. 2.

In Inventive Compound 1-1 of which substituent is bis-biphenyl, HOMO electron cloud is formed except for dibenzofuran, however in Comparative Compound 2 of which substituent is terphenyl, the electron cloud is not formed to the terminal of terphenyl. When examining LUMO electron cloud, difference may be clearly shown. The LUMO electron cloud is formed for dibenzofuran in Inventive Compound 1-1 and is formed for bis-terphenyl in Comparative Compound 2. Accordingly, the energy level values of HOMO and LUMO become different, and the inventive compounds may have a higher LUMO value and a wider band gap. Due to such chemical difference, holes and electrons make charge balance owing to an appropriate EBL role while measuring a device, and light emission is attained not at the interface of a hole transport layer but in the light emitting layer, thereby decreasing a driving voltage and maximizing efficiency and life span.

As described in the results, even though the same core is used, the linker (linear or non-linear) and the kind of the substituent (terphenyl or the substituent of the inventive compound) act as a main factor of the performance improvement of the device of the EBL, different results may be obtained.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

What is claimed is:
1. A compound represented by Formula (7) or (8):

Formula (7)

Formula (8)

wherein
n is an integer of 0 to 4,
m is an integer of 0 to 3,
o and p are an integer of 1 to 5,
$R^1$ and $R^2$ are each independently selected from the group consisting of deuterium, $C_6$-$C_{10}$ aryl group, a fluorenyl group, a $C_1$-$C_{15}$ alkyl group,
in the case where m and n are each 2 or more, $R^1$ and $R^2$ are each in plural being the same or different from each other, and a plurality of $R^1$s and/or a plurality of $R^2$s may combine to each other to form a ring, and
$R^3$ and $R^4$ are each independently a $C_6$-$C_{10}$ aryl group unsubstituted or with deuterium.
2. The compound of claim 1 represented by one of the following compounds:

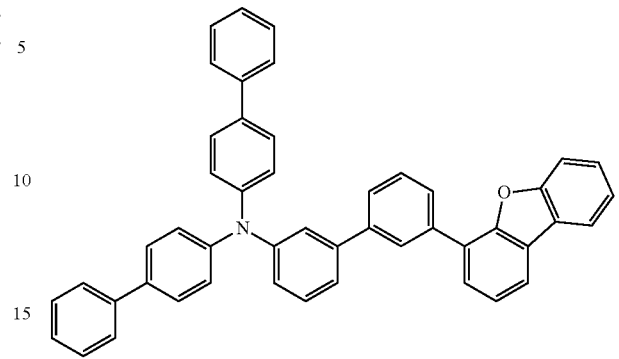

2-1

2-2

2-3

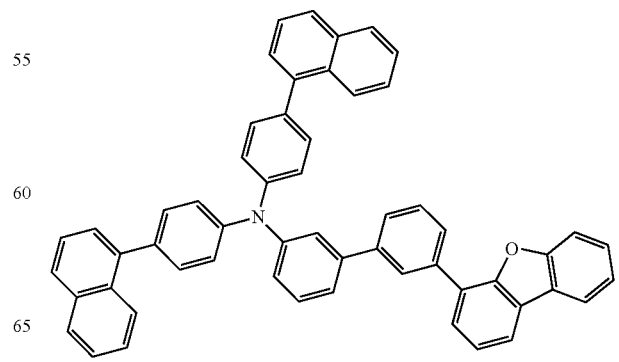

2-4

2-5
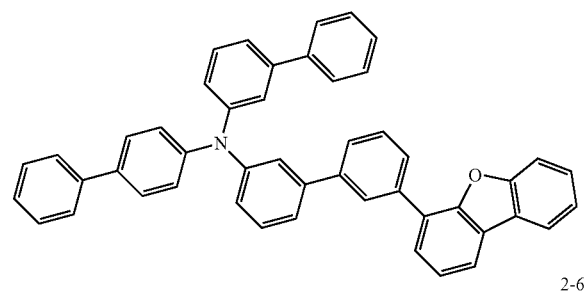
2-6
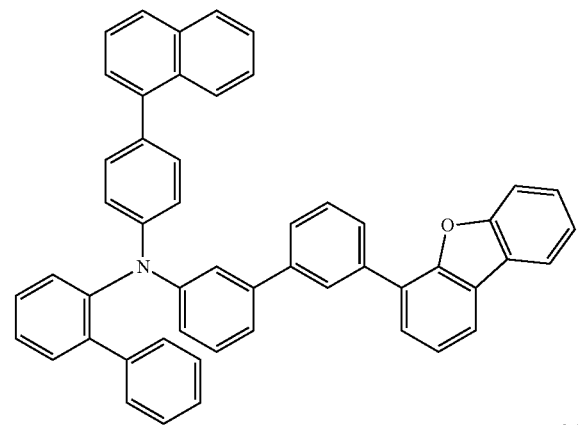
2-7
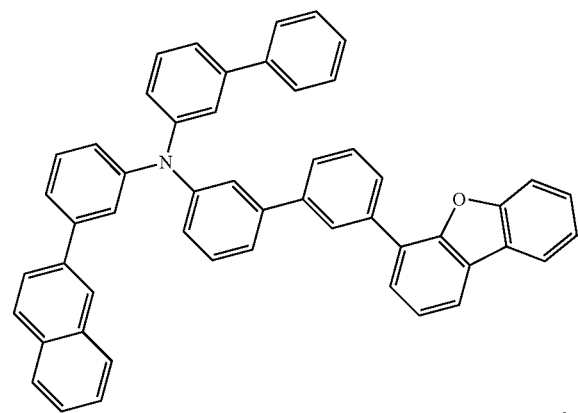
2-8
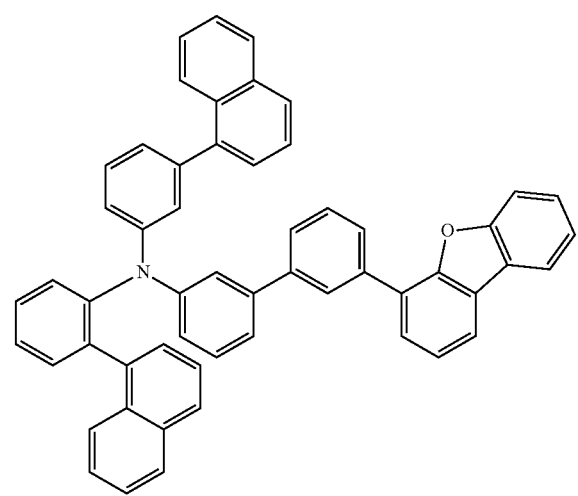
2-9
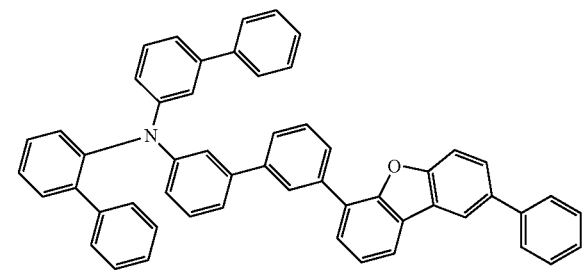
2-10
2-11
2-12

-continued
3-1
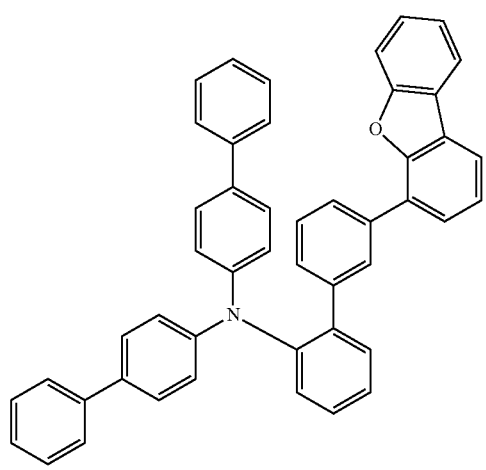
3-2
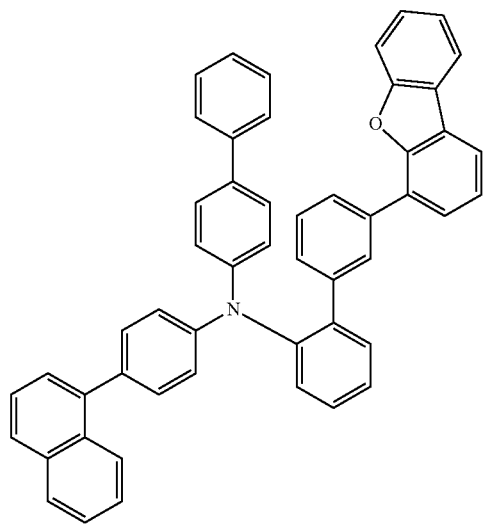
3-3
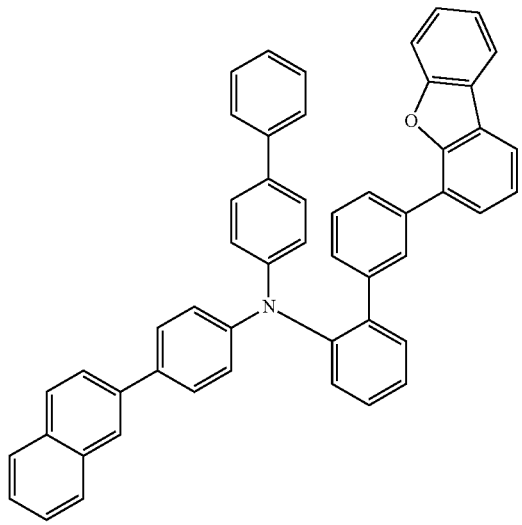
-continued
3-4
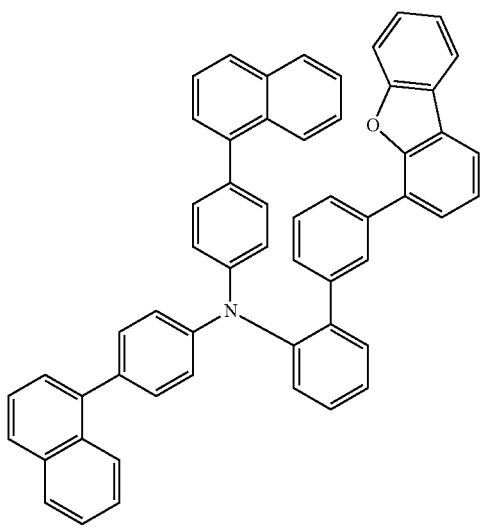
3-5
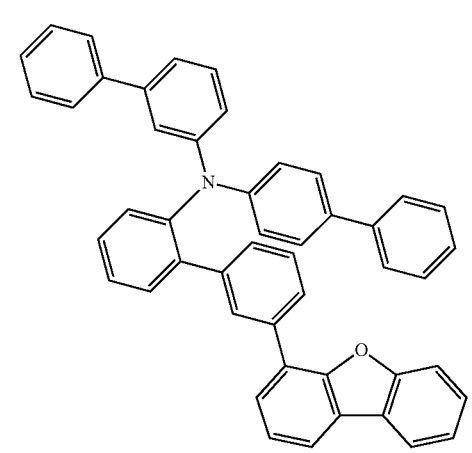
3-6
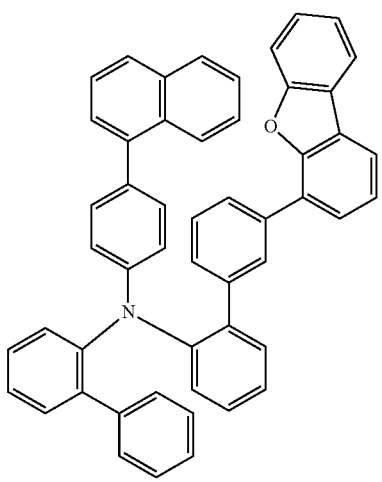

-continued

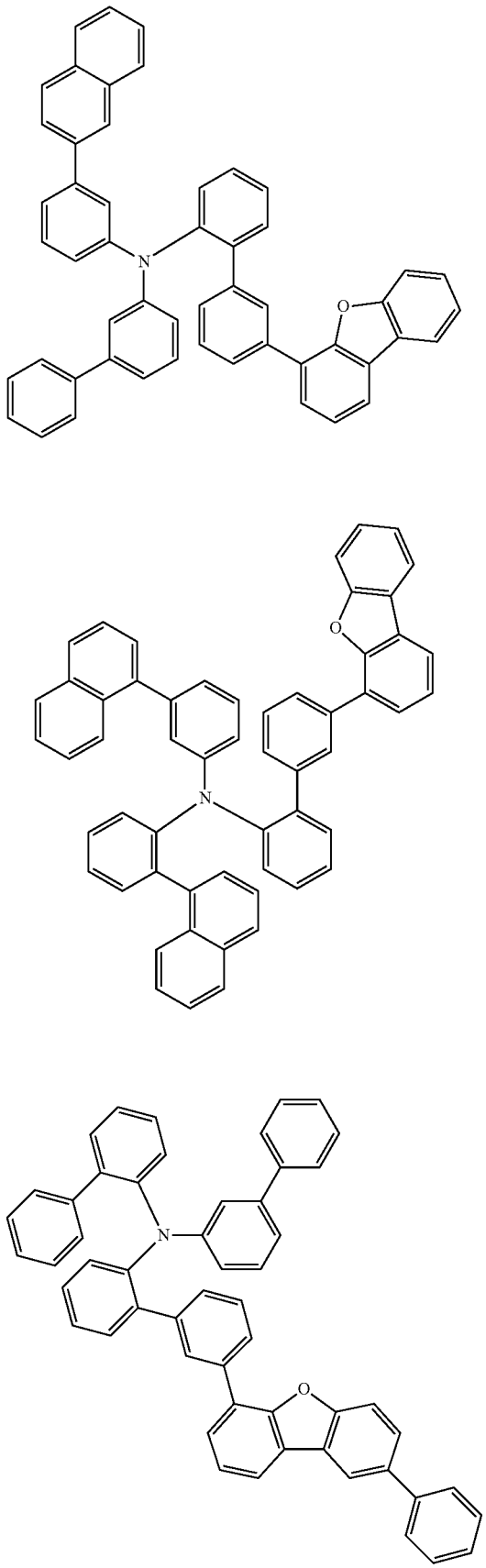

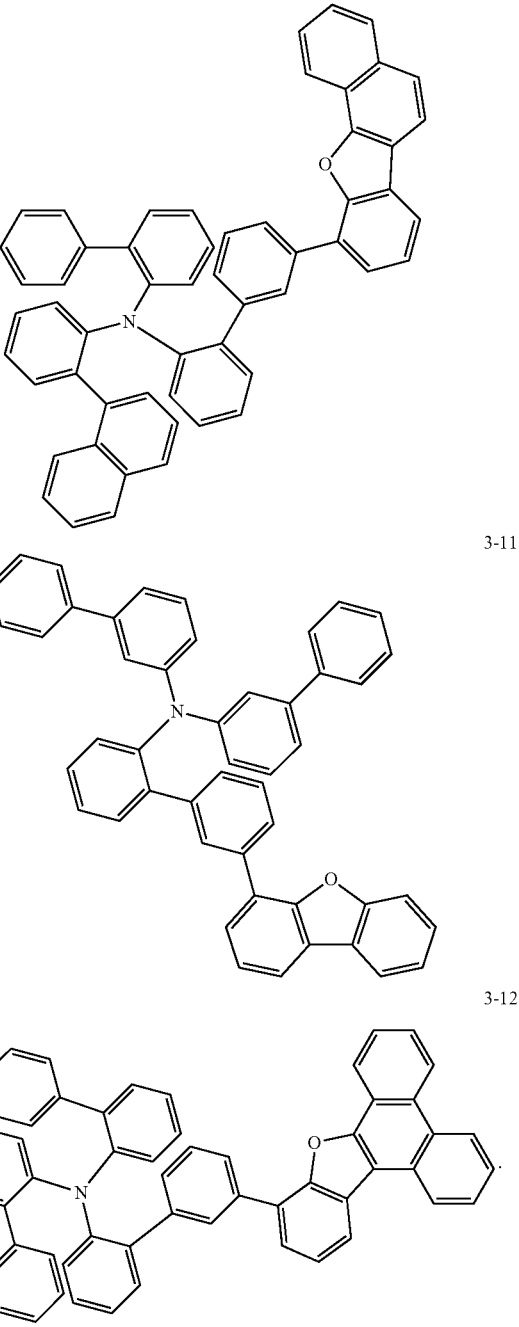

3. An organic electric element comprising: a first electrode; a second electrode; and an organic layer positioned between the first electrode and the second electrode, the organic material layer comprising the compound according to claim 1.

4. The organic electric element of claim 3, wherein the compound is comprised in the organic material layer formed between the first electrode and an light emitting layer.

5. The organic electric element of claim 3, wherein the compound is comprised in an electron blocking layer (EBL) of the organic material layer as a single compound or as a mixture of two or more kinds thereof.

6. The organic electric element of claim 3, wherein the organic material layer is formed by one of a spin coating process, a nozzle printing process, an inkjet printing process, a slot coating process, a dip coating process, and a roll-to-roll process.

7. The organic electric element of claim 3, further comprising a light efficiency enhancing layer formed on one side of the first electrode and/or one side of the second electrode facing the organic material layer.

8. An electronic device comprising a display apparatus comprising the organic electric element according to claim 3; and a driving part configured to drive the display apparatus.

9. The electronic device of claim 8, wherein the organic electric element is an organic light emitting diode (OLED), an organic solar cell, an organic photo conductor, an organic transistor or a device for monochromic or white illumination.

* * * * *